(12) United States Patent
Fumuro et al.

(10) Patent No.: US 7,207,944 B2
(45) Date of Patent: Apr. 24, 2007

(54) BLOOD PRESSURE MONITOR

(75) Inventors: Shinichi Fumuro, Hikone (JP); Koichi Okada, Hikone (JP); Takeshi Kojima, Hikone (JP); Tsuyoshi Yuasa, Hikone (JP); Nobuo Iwai, Hikone (JP)

(73) Assignee: Matsushita Electric Works, Ltd., Kadoma-shi Osaka (JP)

( * ) Notice: Subject to any disclaimer, the term of this patent is extended or adjusted under 35 U.S.C. 154(b) by 0 days.

(21) Appl. No.: 11/062,440

(22) Filed: Feb. 23, 2005

(65) Prior Publication Data

US 2005/0187485 A1 Aug. 25, 2005

(30) Foreign Application Priority Data

| Feb. 24, 2004 | (JP) | ............................. 2004-047492 |
| Feb. 24, 2004 | (JP) | ............................. 2004-047512 |
| Feb. 24, 2004 | (JP) | ............................. 2004-047551 |
| May 25, 2004 | (JP) | ............................. 2004-154565 |

(51) Int. Cl.
*A61B 5/02* (2006.01)

(52) U.S. Cl. ...................................... 600/499; 600/490

(58) Field of Classification Search ......... 600/490–499
See application file for complete search history.

(56) References Cited

U.S. PATENT DOCUMENTS

| 3,935,984 A | | 2/1976 | Lichowsky et al. |
| 4,206,765 A | * | 6/1980 | Huber ........................ 600/490 |
| 4,274,424 A | * | 6/1981 | Kimura et al. .............. 600/499 |
| 4,308,871 A | | 1/1982 | Shouda et al. |
| 5,595,180 A | * | 1/1997 | Ogura et al. ................ 600/499 |
| 5,649,536 A | * | 7/1997 | Ogura et al. ................ 600/493 |

(Continued)

FOREIGN PATENT DOCUMENTS

JP          1-254146          10/1989

(Continued)

OTHER PUBLICATIONS

English Language Abstract of JP 2000-217794.

(Continued)

*Primary Examiner*—Charles A Marmor, II
*Assistant Examiner*—Navin Natnithithadha
(74) *Attorney, Agent, or Firm*—Greenblum & Bernstein, P.L.C.

(57) ABSTRACT

A blood pressure monitor is provided with a box-shaped housing having openings formed in left and right side walls, a cuff transversely arranged in the housing and including an arm entrance and an arm exit at the opposite left and right ends corresponding to the openings. The cuff is formed with a blood flow blocking bag in a specified area. The opposite ends of the cuff is taken up by a cuff take-up drum such that the blood flow blocking bag extends along the outer circumferential surface of the inserted arm at the time of a measurement and a compressed air is supplied to the blood flow blocking bag to block the blood flow. The blood pressure monitor is further provided with at least one of a fastening force adjusting construction for adjusting a force of the cuff to evenly fasten the arm or the like of the measurer, a construction for preventing the epidermis part of the arm from getting in the cuff, a construction for suppressing the consumption of an electric power, and a construction for fixing a measuring position.

10 Claims, 20 Drawing Sheets

U.S. PATENT DOCUMENTS

| | | | |
|---|---|---|---|
| 5,660,182 A * | 8/1997 | Kuroshaki et al. | 600/499 |
| 6,471,657 B2 * | 10/2002 | Sadritabrizi | 600/499 |
| 2002/0120199 A1 | 8/2002 | Ogura et al. | |

FOREIGN PATENT DOCUMENTS

| | | |
|---|---|---|
| JP | 02-37605 | 3/1990 |
| JP | 2000-107140 | 4/2000 |
| JP | 2000-217794 | 8/2000 |
| JP | 3233481 | 9/2001 |
| JP | 3235602 | 9/2001 |

OTHER PUBLICATIONS

English Language Abstract of JP 2000-107140.
English language Abstract of JP 1-254146.
English language Abstract of JP 3275602.
English language Abstract of JP 3233481.
English language Abstract of JP 02-37605.

* cited by examiner

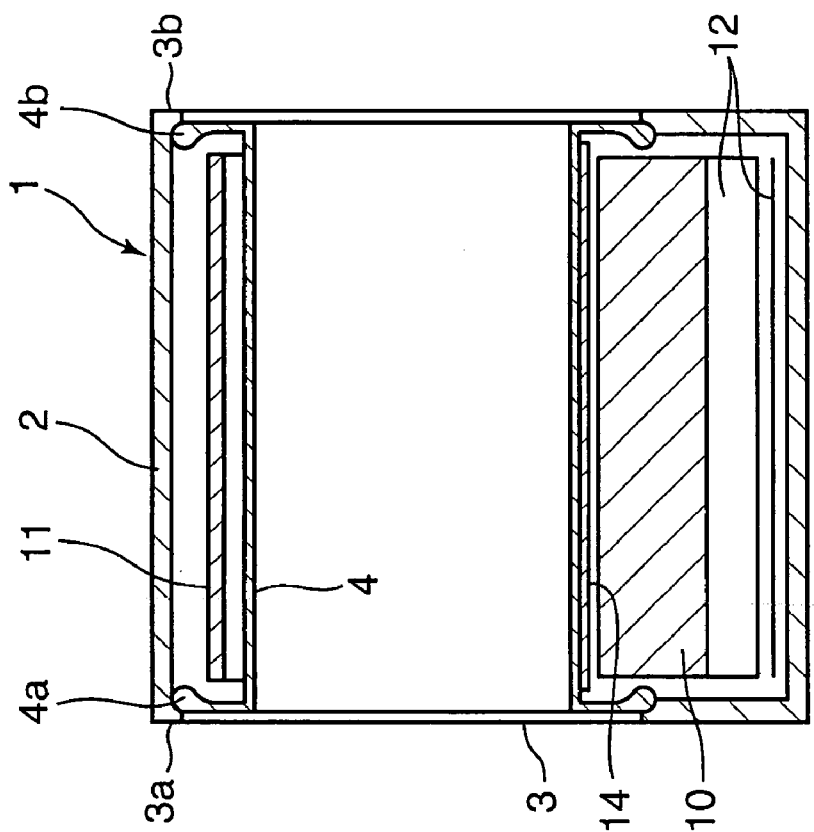
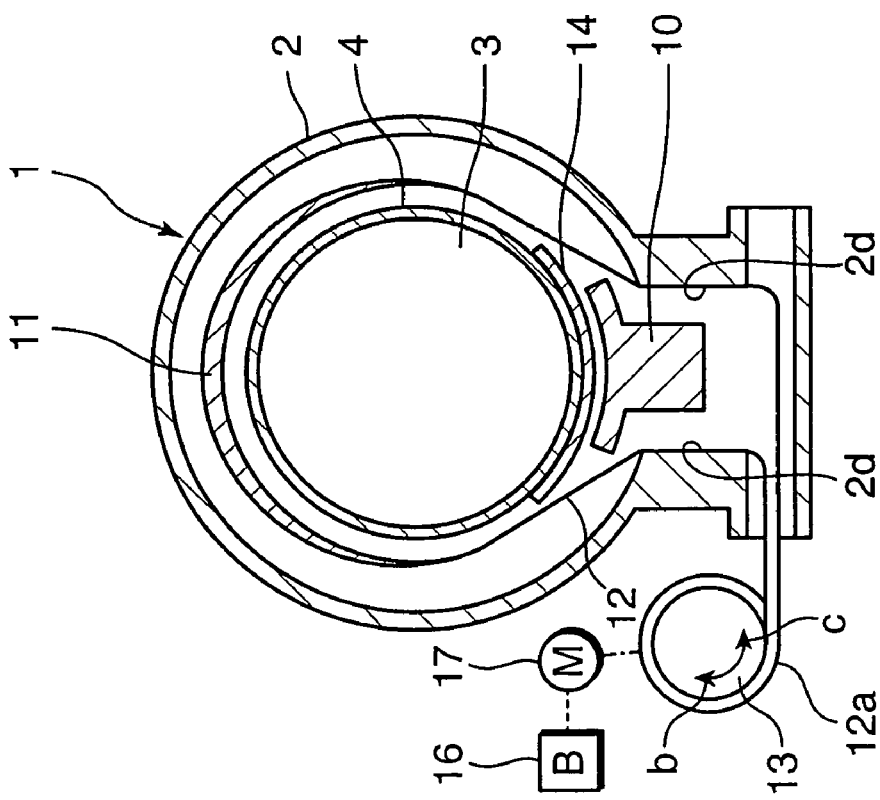

FIG. 7A
FIG. 7B
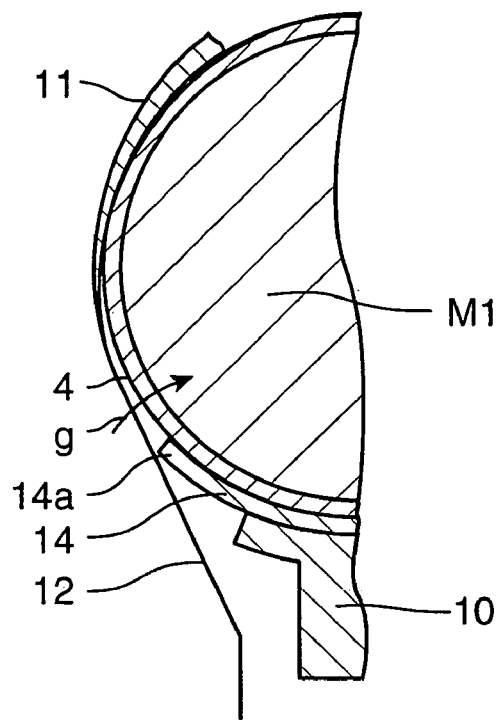
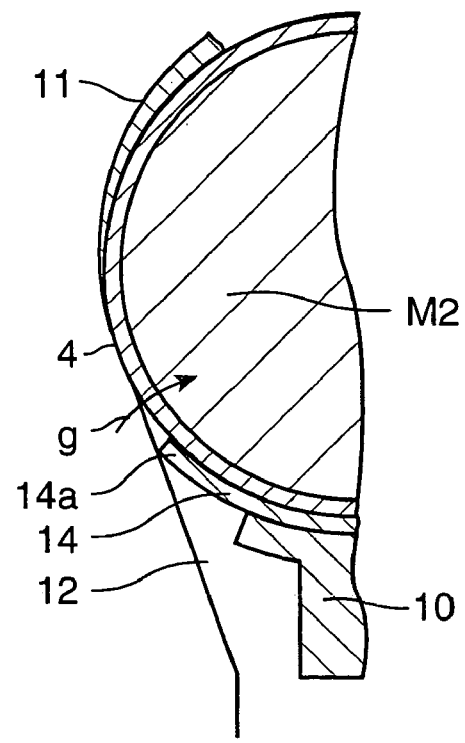
FIG. 8
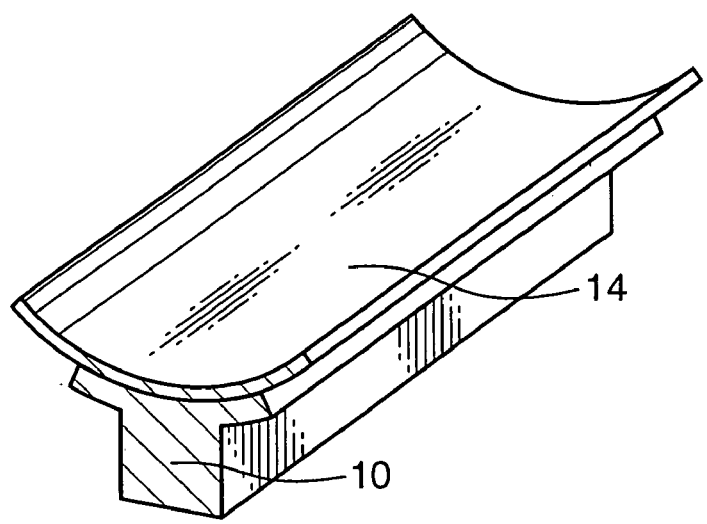

BLOOD PRESSURE MONITOR

BACKGROUND OF THE INVENTION

The present invention relates to a blood pressure monitor for measuring a blood pressure using an arm.

BACKGROUND OF THE INVENTION

For the measurement of a blood pressure, it has been a conventional practice to insert an arm of a measurer into an arm insertion hole formed by a cuff holding a blood flow blocking bag, then to fix the cuff to the arm, and to measure a blood pressure by inflating the blood flow blocking bag to apply a specified pressure (for example, Japanese Unexamined Patent Publication No. H01-254146, Japanese Patent No. 3235602). However, there have been recognized main points to be improved, for example, in order (1) to enable a precise measurement, (2) not to give any feeling of pressure or any feeling of tension of a measurement to a measurer, and (3) to enable an efficient use of a driving energy of a blood pressure monitor. Specifically, there have been the following problems.

An arm to be measured, normally an upper arm is thicker at a shoulder side while being thinner at a wrist side. On the other hand, since a conventional cuff is rectangular, if an attempt is made to fix the cuff to the arm by taking up the cuff by means of a take-up drum, the cuff comes into contact only with the shoulder side of the arm while being not fixed at all at the wrist side. In such a state, no precise blood pressure measurement can be made.

Upon winding the cuff holding the blood flow blocking bag around the arm, an epidermis part of the arm often gets in the cuff. Japanese Patent Publication No. 3233481 proposes a blood pressure monitor in which one end of a cuff holding a blood flow blocking bag is fixed to an arm rest and the other end is coupled to a take-up mechanism to automatically take up the cuff. Japanese Unexamined Utility Model Publication No. H02-37605 proposes a blood pressure monitor of the hand winding type in which a covering member for covering a measurement part at an inserting side of a folded member in order to prevent an epidermis part of an arm from getting in a cuff. However, with the blood pressure monitor having the automatic take-up mechanism, the epidermis part of the arm may be pulled by the cuff being taken up and may get in between lateral portions of the arm rest and the cuff when the cuff is taken up by the automatic take-up mechanism. The blood pressure monitor of the hand winding type has a problem of being inconvenient and taking much labor because the cuff is hand-wound.

On the other hand, in the case of automatically taking up the cuff, a dry battery is normally used as a power supply for driving the take-up drive in view of portability. The dry battery has a limit in capacity. However, there is a large resistance at the time of taking up and rewinding the cuff. In order to enable the dry battery to be efficiently used, there has been a strong demand to maximally suppress this resistance.

Further, it is difficult to know how much an arm should be inserted when a measurer inserts his arm. If the arm is inserted too deeply or too lightly, there is a problem of being unable to make a precise measurement.

SUMMARY OF THE INVENTION

An object of the present invention is to provide a blood pressure monitor which is free from the problems residing in the prior art.

Another object of the present invention is to provide a blood pressure monitor which can evenly press an arm or the like of a measurer.

Still another object of the present invention is to prevent an epidermis part of an arm from getting in a cuff.

Further another object of the present invention is to provide a blood pressure monitor which can suppress the consumption of an electric power.

Still another object of the present invention is to provide a blood pressure monitor which can constantly measure a blood pressure at a fixed measuring position.

According to an aspect of the present invention, a blood pressure monitor comprises a box-shaped housing having openings formed in left and right side walls, and a cuff transversely arranged in the housing and having an arm entrance and an arm exit at the opposite left and right ends corresponding to the openings. The cuff is formed with a blood flow blocking bag in a specified area. At the time of measuring a blood pressure, the opposite ends of the cuff are so taken up by a take-up drum that the blood flow blocking bag extends along the outer circumferential surface of the inserted arm, and the blood flow is blocked by supplying a compressed air to the blood flow blocking bag.

Preferably, the blood pressure monitor may be provided with at least one of a fastening force adjusting construction for adjusting a force of the cuff to evenly fasten the arm or the like of the measurer, a construction for preventing the epidermis part of the arm from getting in the cuff, a construction for suppressing the consumption of an electric power, and a construction for fixing a measuring position.

These and other objects, features, aspects and advantages of the present invention will become more apparent from the following detailed description of the preferred embodiments/examples with reference to the accompanying drawings.

BRIEF DESCRIPTION OF THE DRAWINGS

FIG. 2A is a sectional view taken along the line IIA—IIA of FIG. 1, FIG. 2B is a sectional view taken along the line IIB—IIB of FIG. 1, FIG. 8 is a perspective view of an arm rest having the auxiliary sheet mounted.

DETAILED DESCRIPTION OF THE PREFERRED EMBODIMENTS OF THE INVENTION

Figure 1:
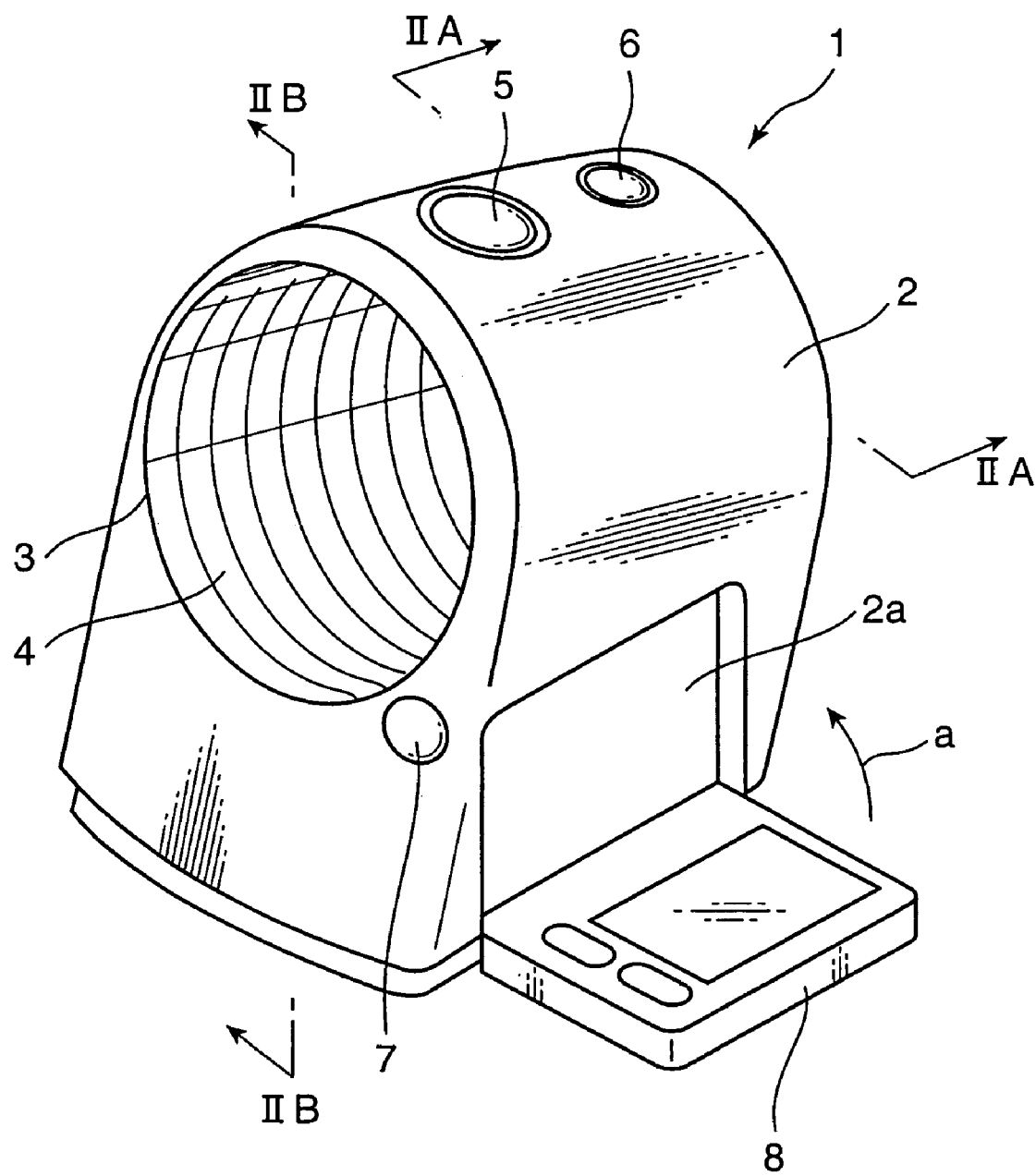
FIG. 1 is a perspective view showing the construction of a blood pressure monitor according to an embodiment of the invention.

A blood pressure monitor according to an embodiment of the present invention is shown in FIG. 1. This blood pressure monitor 1 has a compact and simple construction for home use, wherein a box-shaped housing 2 is formed with an arm inserting hole 3 penetrating the housing 2 along forward and backward directions and a soft tubular cuff ring 4 into which an arm is inserted is arranged in the arm inserting hole 3. The cuff ring 4 is made of a fabric of a polyethylene or the like.

A start/end switch 5 and an emergent exhaust switch 6 are provided at the top of the housing 2, an opening button 7 for opening a display panel 8 is provided at the front side, and the display panel 8 openable and closable by a hinge is provided at a side. Upon being closed in a direction of arrow "a" from an open position shown in FIG. 1, the display panel 8 is accommodated and locked at a closed position by being fitted into a recess 2a formed in a side surface of the housing 2. When the opening button 7 is pushed, the display panel 8 is unlocked and can be opened to the open position.

A pump, an exhaust valve, a pressure sensor and the like are provided in the housing 2 and connected by a pipe for supplying an air to a blood flow blocking bag 11 to be described later, and have operation timings thereof controlled by a control unit.

As shown in FIGS. 2A and 2B, an arm rest 10 substantially T-shaped in front view is provided below the arm inserting hole 3 of the housing 2, wherein the upper surface of this arm rest 10 is formed into a curve in conformity with a curvature of the arm inserting hole 3. This arm rest 10 is a hard molded article made of, for example, an ABS resin.

Inside the arm inserting hole 3, a cuff 12 holding the blood flow blocking bag 11 is arranged at an upper part and opposite end portions 12a thereof are coupled to a take-up drum 13 provided at a bottom part of the housing 2 by way of the opposite sides of the arm rest 10. The cuff 12 is, for example, a flexible plastic sheet, and a portion thereof holding the blood flow blocking bag 11 serves also as a clip board for suppressing the inflation of the blood flow blocking bag 11.

The take-up drum 13 is driven in forward and backward directions by an electric motor having a commercially available dry battery 16 set in the housing 2 as a power supply. The take-up drum 13 is rotated in a direction of arrow "b" to take up the cuff 12 upon being driven in forward direction while being rotated in a direction of arrow "c" to rewind the cuff 12 upon being driven in reverse direction.

The cuff ring 4 is arranged between the arm rest 10 and the cuff 12 with an insertion-side ring portion 4a engaged with an arm entrance 3a of the arm inserting hole 3 and an exit-side ring portion 4b engaged with an arm exit 3b of the arm inserting hole 3, thereby covering the inner circumferential surface of the arm inserting hole 3.

A flexible auxiliary sheet 14 having a rectangular shape longer along circumferential direction than the upper surface of the arm rest 10 may be so mounted on a lower part of the outer surface of the cuff ring 4, for example, by adhesive as to face the upper surface of the arm rest 10.

In this blood pressure monitor 1, when the start/end switch 5 is turned on with an arm inserted in the cuff ring 4 of the arm inserting hole 3 of the housing 2 and placed on the arm rest 10, the take-up drum 13 is driven in forward direction, thereby taking up the opposite end portions 12a of the cuff 12. As a result, the arm is pressed against the arm rest 10 via the cuff ring 4 while the blood flow blocking bag 11 is wound around the arm via the cuff ring 4.

When the blood flow blocking bag 11 is wound around the arm with a specified winding force, air is supplied from the pump to the blood flow blocking bag 11 via the pipe, thereby pressing the arm to block the blood flow through the artery until the winding force of the blood flow blocking bag 11 reaches a specified pressure. When the pressure sensor confirms an arrival at the specified pressure, the pump is stopped and the air in the blood flow blocking bag 11 is exhausted by means of an exhaust valve to reduce the pressure at a constant rate. Thereafter, the take-up drum 13 is driven in reverse direction to rewind the cuff 12.

A pulse wave of the artery is extracted by a filter or the like when the arm is pressed by the blood flow blocking bag 11, and a blood pressure value is calculated using a specified algorithm and the result is displayed on the display panel 8.

Figure 3A:
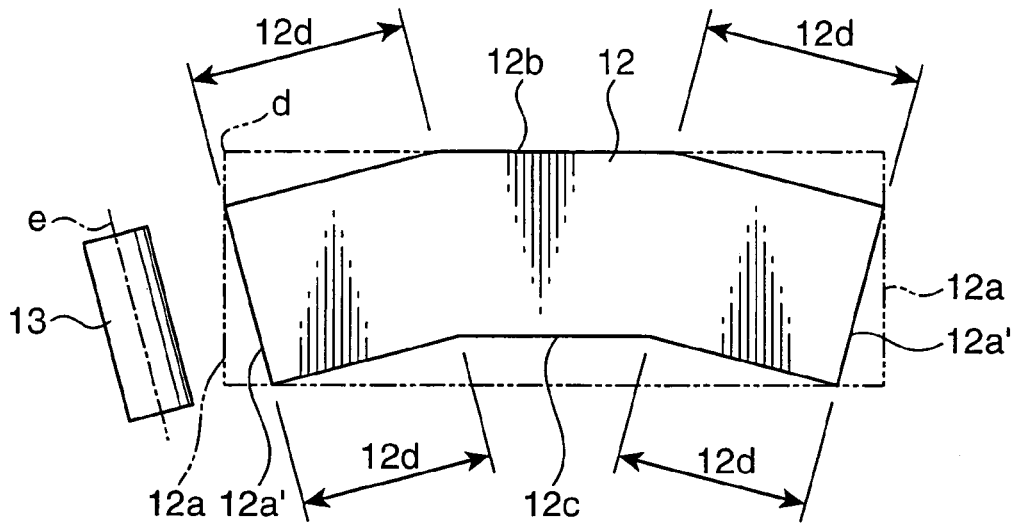
FIG. 3A is a development view of a cuff and a take-up drum used in the blood pressure monitor of FIG. 1.
Figure 3B:
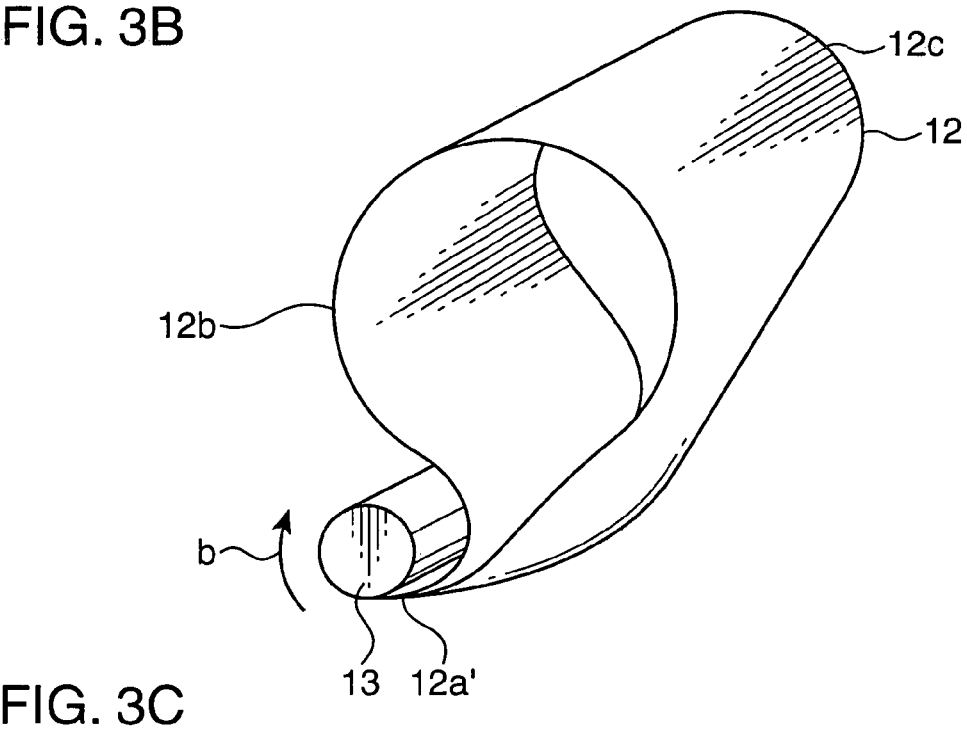
FIG. 3B is a perspective view showing a taken-up state of the cuff.
Figure 3C:
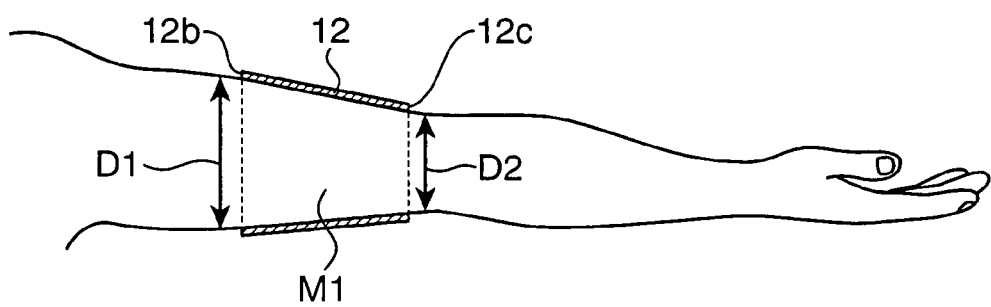
FIG. 3C is a sectional view showing a state where the cuff is wound around an upper arm.

On the other hand, as shown in FIGS. 3A, 3C, the cuff 12 is not rectangle-shaped as shown in phantom line "d", but is shaped such that opposite longitudinal end portions 12a' of the cuff 12 are inclined as shown in solid line. Opposite side portions 12b, 12c in the middle having opposite widthwise end portions 12d of the cuff 12 are so shaped as to extend along a direction normal to the longitudinal axis of the drum 13. In other words, the cuff 12 appears to be fan-shaped.

The inclined opposite end portions 12a' of the cuff 12 are coupled to the take-up drum 13 in parallel with a longitudinal direction "e" of the take-up drum 13 with the end edges thereof put together aligned.

When being taken up by rotating the take-up drum 13 having the inclined opposite end portions 12a' of the cuff 12 coupled thereto in a direction of arrow "b", the cuff 12 is wound substantially into the shape of a conical tube larger at the outer end portion 12b and smaller at the inner end portion 12c since the entire length of the outer end portion 12b is longer than that of the inner end portion 12c.

Accordingly, if a thicker side D1 of an upper arm M1 is placed at the outer end portion 12b and a thinner side D2 is placed at the inner end portion 12c as shown in FIG. 3C, there is no clearance between the cuff 12 and the upper arm M1 and, hence, the upper arm M1 can be evenly pressed by the blood flow blocking bag 11. Therefore, measurement precision can be improved. Further, an inexpensive production cost can be realized since the arm can be evenly pressed only by changing the outer shape of the cuff 12.

Since the opposite longitudinal end portions 12d in the middle of the cuff 12 are so shaped as to extend along the direction normal to the longitudinal direction of the take-up drum 13, this can prevent the cuff 12 from being taken up while being displaced along the longitudinal direction of the take-up drum 13 when the cuff 12 is taken up by the take-up drum 13.

Figure 4A:
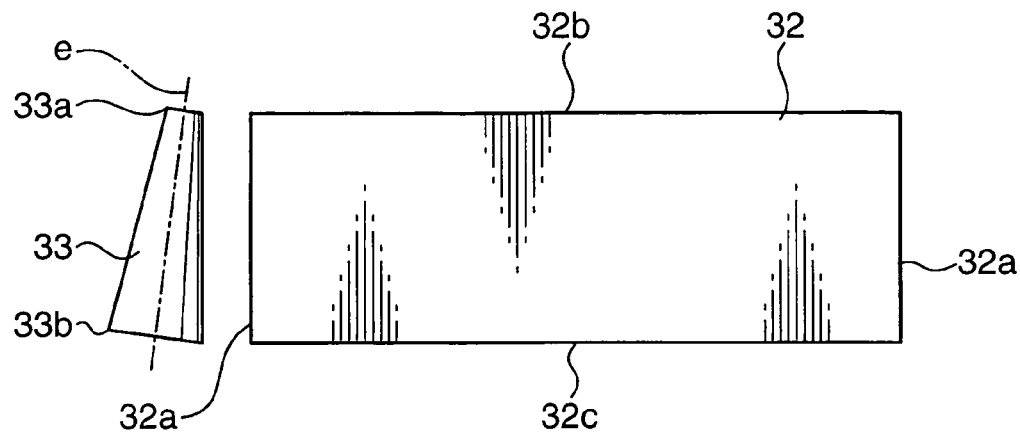
FIG. 4A is a development view showing a modification of the cuff and the take-up drum used in the blood pressure monitor of FIG. 1.
Figure 4B:
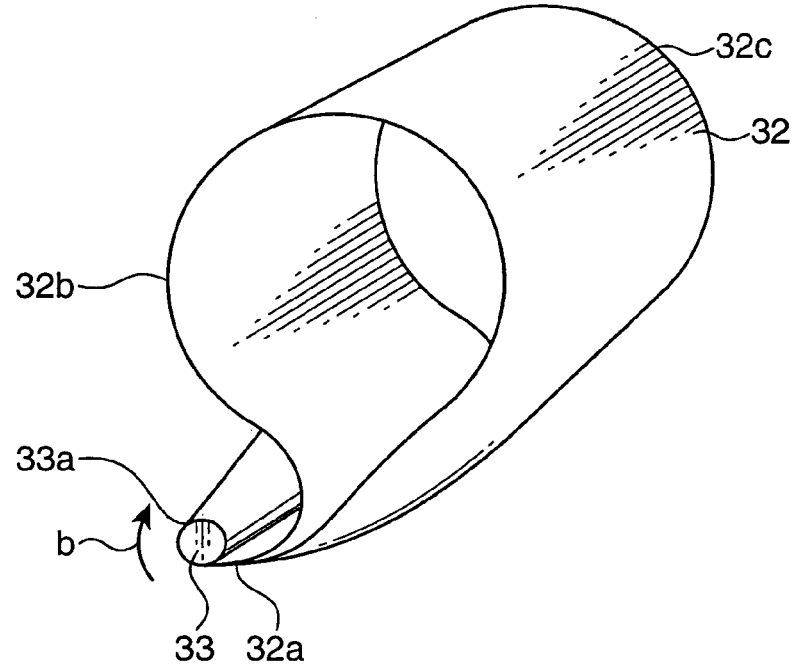
FIG. 4B is a perspective view showing a taken-up state of the cuff of FIG. 4A.
Figure 4C:
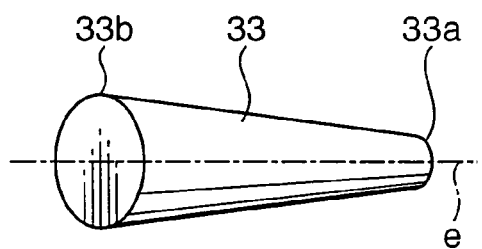
FIG. 4C is a perspective view of the take-up drum used for the cuff of FIG. 4A.

FIGS. 4A to 4C show a modification of the cuff used in this embodiment. Although a modified cuff 32 is rectangle-shaped, the take-up drum 33 is formed to have a conical shape and opposite end portions 32a of the cuff 32 are coupled in parallel to the conical surface of the take-up drum 33. Similar to the above cuff 12, this cuff 32 is provided with the blood flow blocking bag 11 at an upper side and is made of a flexible plastic sheet.

When being taken up by rotating the conically shaped take-up drum 33 having the opposite end portions 32a of the cuff 32 coupled thereto in a direction of arrow "b", the cuff 32 is wound substantially into such a conical tube larger at a widthwise end portion 32b at a thinner side 33a of the drum and smaller at a widthwise end portion 32c at a thicker side 33b since the thinner side 33a of the take-up drum 33 has a shorter circumference than the thicker side 33b.

Accordingly, when the thicker side D1 of the upper arm M1 is placed at the end portion 32b corresponding to the thinner side 33a of the take-up drum 33 and the thinner side D2 is placed at the end portion 32c corresponding to the thicker side 33b of the take-up drum 33 similar to the state shown in FIG. 3C, there is no clearance between the cuff 32 and the upper arm M1 and, hence, the upper arm M1 can be evenly pressed by the blood flow blocking bag 11. Therefore, measurement precision can be improved. Further, an inexpensive production cost can be realized since the arm can be evenly pressed only by changing the outer shape of the take-up drum 33.

Figure 5A:
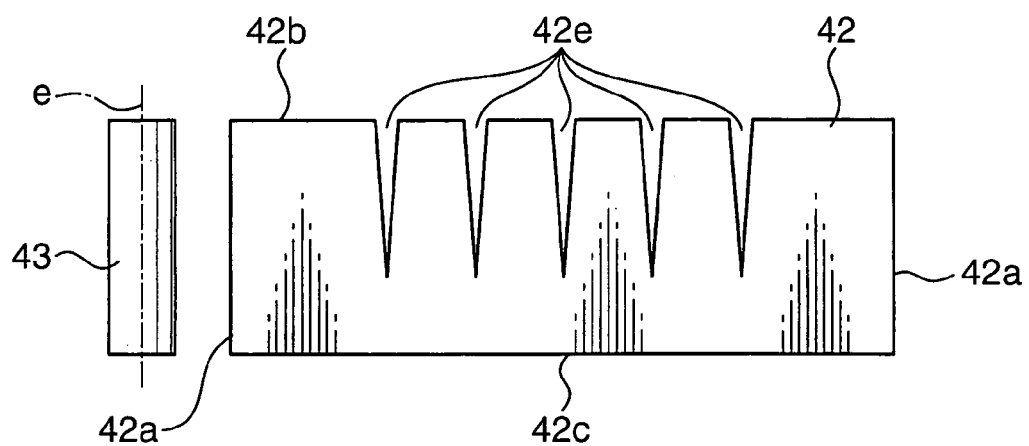
FIG. 5A is a development view showing another modification of the cuff and the take-up drum used in the blood pressure monitor of FIG. 1.
Figure 5B:
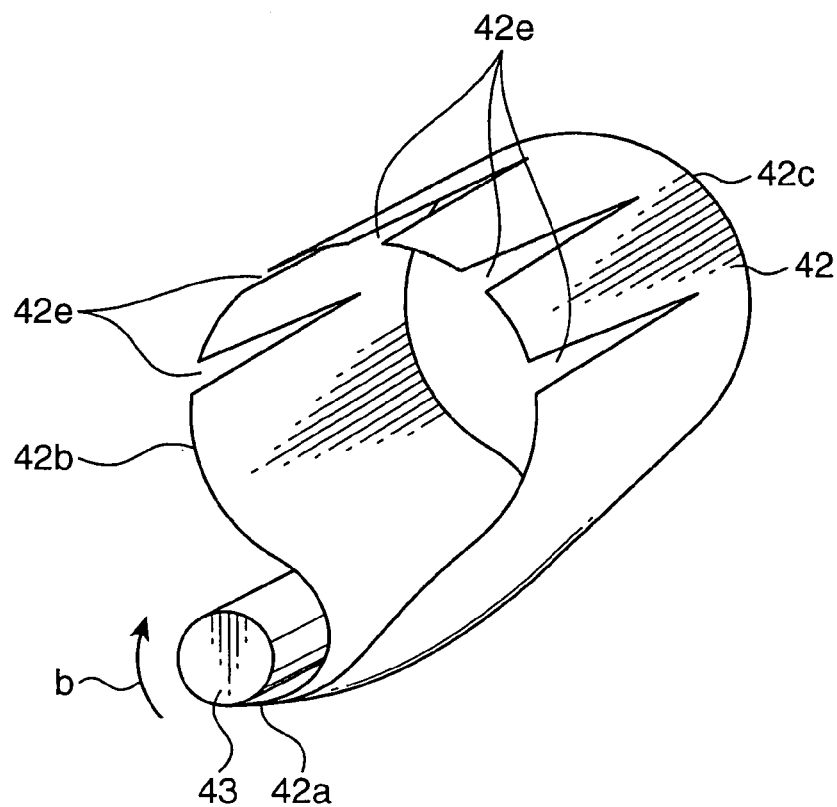
FIG. 5B is a perspective view showing a taken-up state the cuff of FIG. 5A.

FIGS. 5A and 5B show a modification of the cuff used in this embodiment. Although a modified cuff 42 is rectangle-shaped, V-shaped slits or cuts 42e extending toward an other widthwise end portion 42c are formed at specified intervals along longitudinal direction at one widthwise end portion 42b of the cuff 42. Similar to the cuff 12, this cuff 42 is provided with the blood flow blocking bag 11 at an upper side and is made of a flexible plastic sheet.

When being taken up by rotating a take-up drum 43 having opposite end portions 42a of the cuff 42 coupled thereto in a direction of arrow "b", the cuff 42 can be wound substantially into such a conical tube larger at the widthwise end portion 42b formed with the slits 42e and smaller at the widthwise end portion 42c having no slit 42e since the widthwise end portion 42b formed with the slits 42e has a better stretchability or elongation than the widthwise end portion 43c having no slit 42e.

Accordingly, when the thicker side D1 of the upper arm M1 is placed at the end portion 42b having the slits 42e and the thinner side D2 is placed at the end portion 42c having no slit 42e similar to the state shown in FIG. 3C, there is no clearance between the cuff 42 and the upper arm M1 and, hence, the upper arm M1 can be evenly pressed by the blood flow blocking bag 11. Therefore, measurement precision can be improved. Further, an inexpensive production cost can be realized since the arm can be evenly pressed only by forming the cuff 42 with the slits 42e.

Figure 6A:
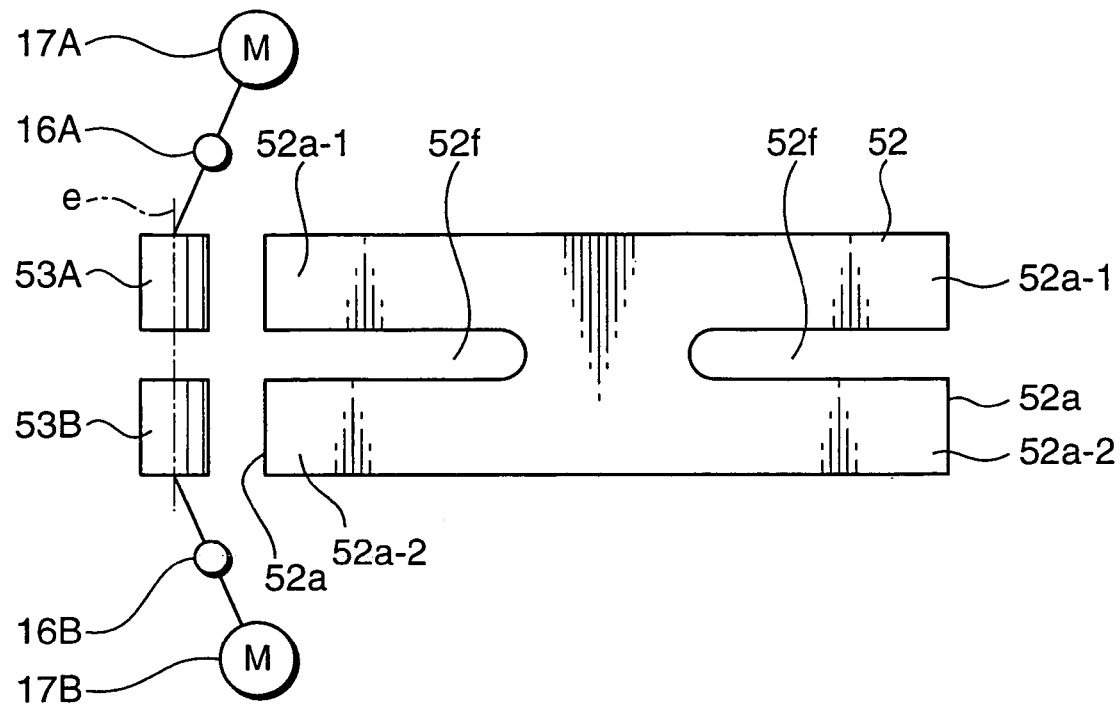
FIG. 6A is a development view showing still another modification of the cuff and the take-up drum used in the blood pressure monitor of FIG. 1.
Figure 6B:
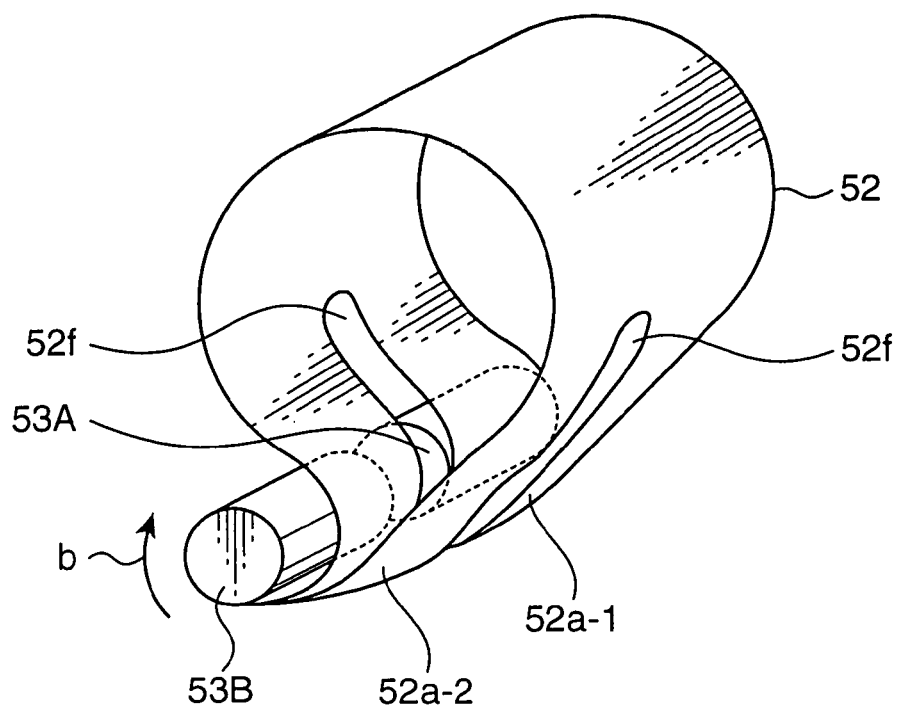
FIG. 6B is a perspective view showing a taken-up state the cuff of FIG. 6A, FIGS. 7A and 7B are sectional views showing a used state of an auxiliary sheet used in the blood pressure monitor of FIG. 1.

FIGS. 6A and 6B show another modification of the cuff used in this embodiment. Although a modified cuff 52 is rectangle-shaped, a slit. 52f is formed in each end portion 52a to divide this end portion 52a into two sections along widthwise direction, two take-up drums 53A, 53B are provided and constructed to independently take up the cuff 52 via clutches 16A, 16B and electric motors 17A, 17B, and divided end portions 52a-1 and 52a-2 of the cuff 52 are respectively coupled to the take-up drums 53A, 53B at the same sides. Similar to the cuff 12, this cuff 52 is provided with the blood flow blocking bag 11 at an upper side and is made of a flexible plastic sheet.

When the cuff 52 is taken up by rotating the take-up drums 53A, 53B coupled to the corresponding end portions 52a-1, 52a-2 of the cuff 52 divided into two sections in a direction of arrow "b" via the clutches 16A, 16B and the electric motors 17A, 17B, the divided end portions 52a-1, 52a-2 of the cuff 52 are independently wound by the take-up drums 53A, 53B.

Accordingly, the cuff 52 can be wound substantially into a conical tube similar to the state shown in FIG. 3C by letting the take-up drum 53A at the thinner side of the upper arm M1 continue to take up the cuff 52 even if a load acting on the take-up drum 53B corresponding to the end portions 52a-2 at the thicker side D1 of the upper arm M1 increases to turn the clutch 16B off, thereby stopping taking up the cuff 52. Thus, there is no clearance between the cuff 52 and the upper arm M1 and, hence, the upper arm M1 can be evenly pressed by the blood flow blocking bag 11. Therefore, measurement precision can be improved.

Although the foregoing embodiments are described with the upper arm M1 as a measurement part, a wrist M2 can be used as a measurement part.

FIGS. 7A and 7B show a mounted state of the auxiliary sheet 14. As described above, the cuff ring 4 is arranged between the arm rest 10 and the cuff 12 and covers the inner circumferential surface of the arm inserting hole 3 by being engaged with the arm entrance 3a and the arm exit 3b.

Figure 9:
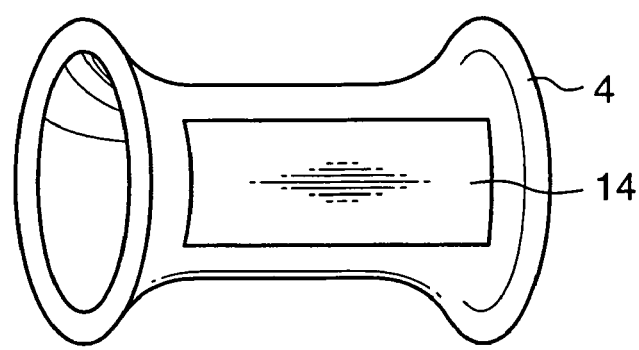
FIG. 9 is a perspective view showing a cuff ring having the auxiliary sheet adhered thereto.
Figure 10:
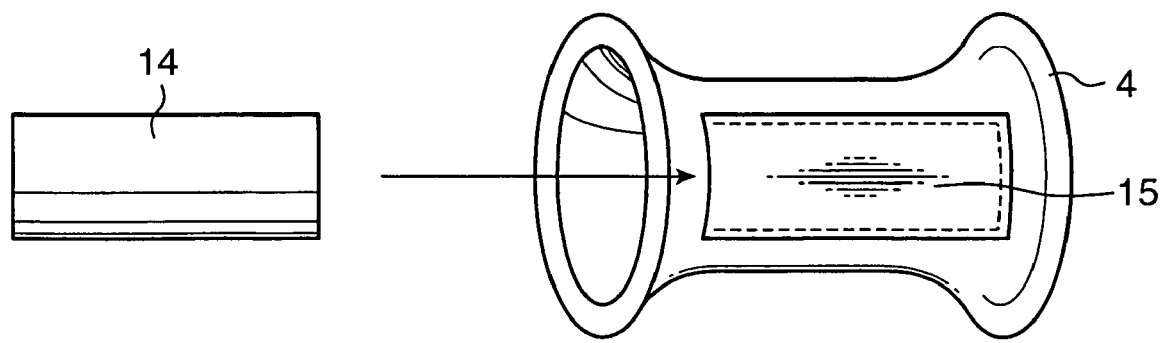
FIG. 10 is a perspective view showing the auxiliary sheet and the cuff ring including a bag-shaped accommodating portion.

The auxiliary sheet 14 is mounted to the cuff ring 4 as shown in FIG. 9 by an adhesive or the like. The auxiliary sheet 14 is mounted at such a position as to face the upper surface of the arm rest 10. The width (i.e., length along the circumferential direction of the cuff ring 4) of the auxiliary sheet 14 is larger than the width (i.e., length along the circumferential direction of the cuff ring 4) of the upper surface of the arm rest 10. The auxiliary sheet 14 is preferably a PET (polyethylene terephthalate) sheet having a thickness of about 0.5 mm, but may be a metallic sheet having a spring property. It should be noted that the auxiliary sheet 14 may be mounted on the upper surface of the arm rest 10 by an adhesive or screws as shown in FIG. 8.

With the above construction, when the start/end switch 5 is turned on with an arm inserted in the cuff ring 4 of the arm inserting hole 3 of the housing 2 and placed on the arm rest 10, the take-up drum 13 is driven in forward direction, thereby taking up the opposite end portions 12a of the cuff 12. As a result, the arm is pressed against the arm rest 10 via the cuff ring 4 while the blood flow blocking bag 11 is wound around the arm via the cuff ring 4.

At this time, the flexible auxiliary sheet 14 longer along circumferential direction than the arm rest 10 is pressed against the cuff 12 whose width is narrowed as the cuff 12 is taken up, whereby opposite end portions 14a along the circumferential direction rise (see arrow "g") to cover the opposite sides of the arm M1, M2 inserted into the cuff ring 4. This can prevent the epidermis part of the arm M1, M2 from being pulled by the cuff 12 being taken up to get in between the cuff ring 4 and the lateral portions of the arm rest 10.

FIG. 7A shows an example of the thicker arm M1 and FIG. 7B shows an example of the thinner arm M2. Since the opposite end portions 14a of the auxiliary sheet 14 fit and rise along the arm M1, M2 regardless of the thicker arm M1 or the thinner arm M2, the epidermis part does not get caught up in either case.

Although the auxiliary sheet 14 is adhered to the outer surface of the cuff ring 4 in the foregoing embodiment, a bag-shaped accommodating portion or pocket 15 stitched at three sides may be provided on the outer surface of the cuff ring 4 and the auxiliary sheet 14 may be inserted and accommodated into this bag-shaped accommodating portion 15. In such a case, an entrance portion is stitched at points to prevent the auxiliary sheet 14 from coming out after the auxiliary sheet 14 is accommodated into the bag-shaped accommodating portion 15.

If the auxiliary sheet 14 is accommodated into the bag-shaped accommodating portion 15 of the cuff ring 4 in this way, problems that the auxiliary sheet 14 comes out of the cuff ring 4 and the mounted position of the auxiliary sheet 14 is displaced are less likely to occur as compared to a case where the auxiliary sheet 14 is adhered.

Figure 11A:
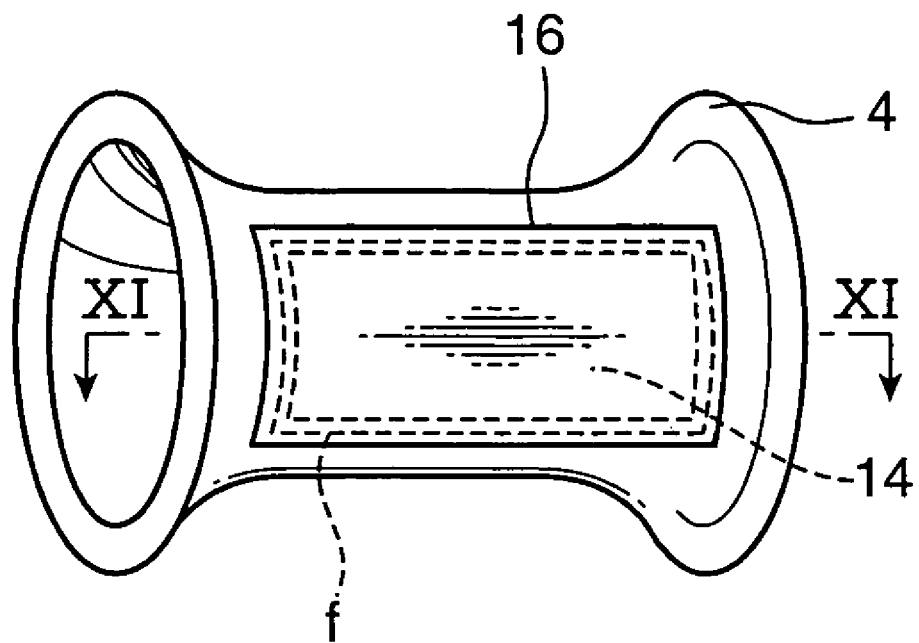
FIG. 11A is a perspective view showing the cuff ring having the auxiliary sheet stitched along an outer contour.
Figure 11B:
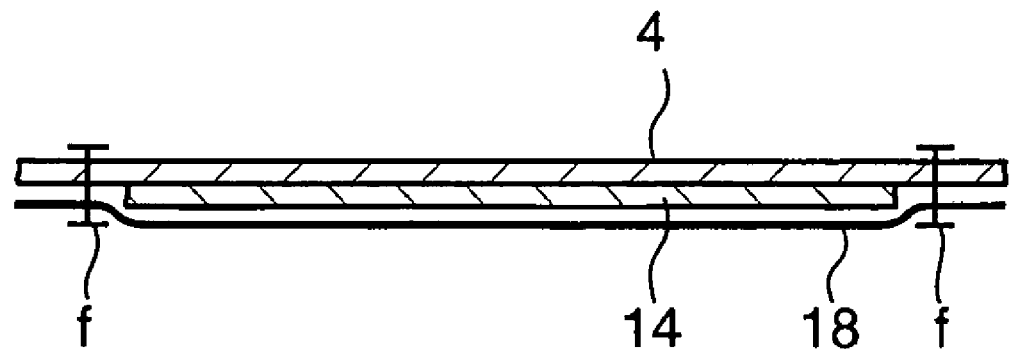
FIG. 11B is a sectional view taken along the line XI—XI of FIG. 11A.

Further, if the auxiliary sheet 14 is placed on the outer surface of the cuff ring 4, a sheet 18 is placed on the auxiliary sheet 14 and the cuff ring 4 and the sheet 18 are stitched "f" along the outer contour of the auxiliary sheet 14 as shown in FIGS. 11A and 11B, there is no likelihood of displacing the mounted position of the auxiliary sheet 14. It should be noted that the auxiliary sheet 14 can be directly stitched with the cuff ring 4 by placing the auxiliary sheet 14 on the outer surface of the cuff ring 4.

Figure 12A:
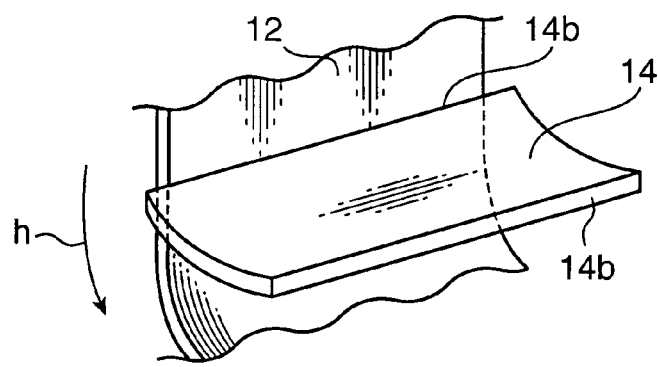
FIG. 12A is a perspective view showing a relationship between an auxiliary sheet having straight edges and the cuff.
Figure 12B:
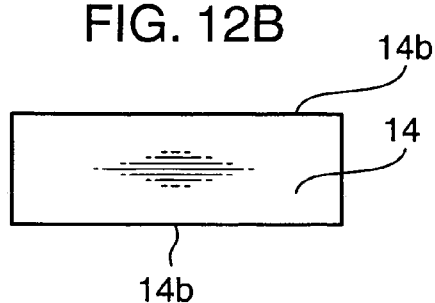
FIG. 12B is a plan view of such an auxiliary sheet.

Since the auxiliary sheet 14 is rectangular and edges 14b toward the cuff 12 are formed to be straight as shown in FIGS. 12A and 12B, the edges 14b of the auxiliary sheet 14 are entirely in contact with the cuff 12 being taken up in a direction of arrow "h". Thus, a winding resistance of the cuff 12 increases.

Figure 13A:
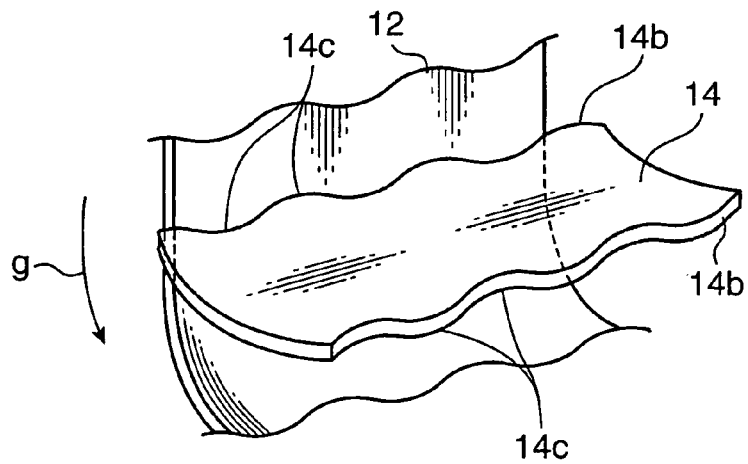
FIG. 13A is a perspective view showing a relationship between an auxiliary sheet having projected and recessed edges and the cuff.
Figure 13B:
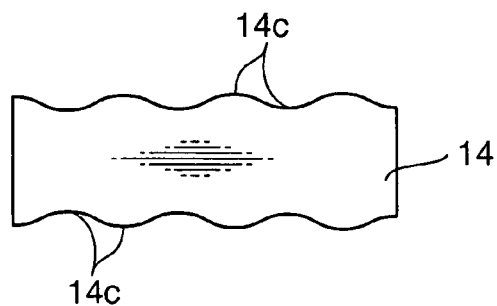
FIG. 13B is a plan view of such an auxiliary sheet.

The winding resistance can be considerably reduced by forming projected and recessed portion portions 14c in plan view at the edges 14b of the auxiliary sheet 14 toward the cuff 12 as shown in FIGS. 13A, 13B.

Accordingly, only the projected portions of the projected and recessed portion portions 14c are in contact with the cuff 12 being take up to reduce a contact area. Thus, the winding resistance of the cuff 12 can decrease to suppress the consumption of an electric power of a dry battery used for the electric motor (not shown) for driving the take-up drum 13.

Figure 14A:
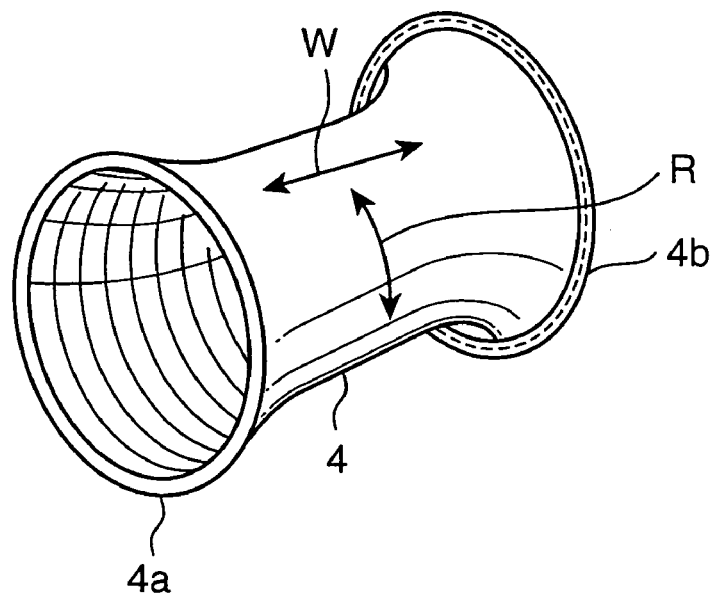
FIG. 14A is a perspective view showing the cuff ring used in the blood pressure monitor of FIG. 1.

Next, the detailed construction of the cuff ring 4 is described with reference to FIGS. 14A and 14B. The cuff ring 4 is made of a stretch material stretchable at least along longitudinal direction W. This does not mean, however, that the cuff ring 4 may not be stretchable along circumferential direction R. The stretch material is preferably stretchable both along longitudinal direction W and circumferential direction R, but is sufficient if it is stretchable at least along longitudinal direction W in view of a material cost. With such a construction of the cuff ring 4, the winding resistance can be reduced.

The stretch material may be the one made of synthetic fibers such as spandex fibers or the one rendered to have stretchability by applying a heating treatment after weaving. Either one may be used. For example, a stretch material having a stretch ratio of 2 at a load of 100 g may be suitably used.

Figure 14B:
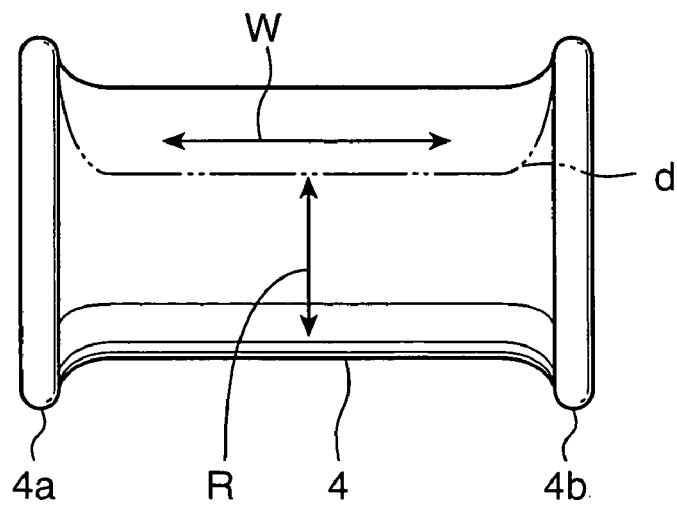
FIG. 14B is a front view of the cuff ring.

Since having a large stretch ratio at least along longitudinal direction, the cuff ring 4 is likely to considerably elongate along longitudinal direction W as shown in phantom line "d" in FIG. 14B when the cuff ring 4 has its diameter reduced by the cuff 12 at the time of taking up the cuff 12. Since resistance is remarkably reduced during this elongation, the consumption of the electric power by the electric motor 17 for driving the take-up drum 13 can be suppressed. Further, the cuff ring 4 contracts to return to its initial shape at the time of increasing the diameter of the cuff 12, its appearance is better.

Figure 15A:
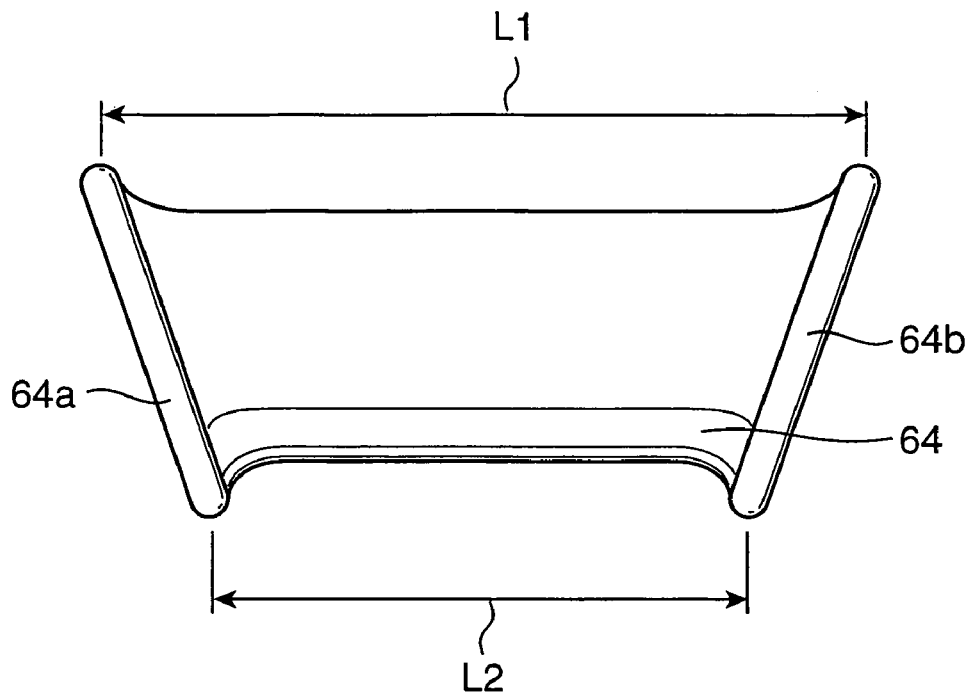
FIG. 15A is a perspective view showing a modification of the cuff ring.
Figure 15B:
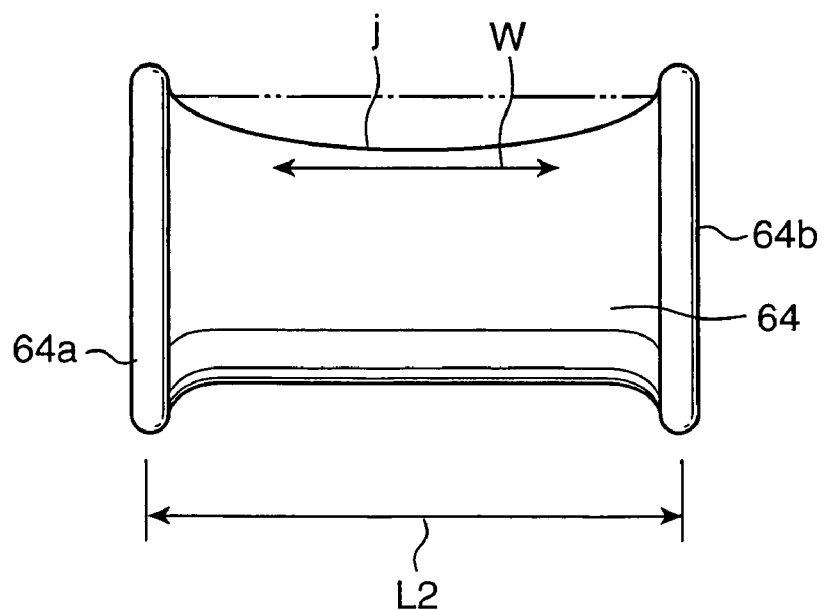
FIG. 15B is a front view showing another modification of the cuff ring.

FIGS. 15A, 15B show a modification of the cuff ring. This modified cuff ring 64 is such that length L1 of the upper side of the cuff ring 64 where the blood flow blocking bag 11 is provided is set to be longer than length L2 of the lower side as shown in FIG. 15A, and the longer upper side having the length L1 is loosened as shown in solid line "j" in FIG. 15B when the cuff ring 64 is assembled into the housing 2. With such a construction, since the upper side of the cuff ring 64 where the blood flow blocking bag 11 is provided is largely loosened, the cuff ring 64 is likely to be considerably loosened along longitudinal direction W as shown in solid line "j" in FIG. 15B when the diameter of the cuff ring 64 is reduced by the cuff 12 at the time of taking up the cuff 12. Since resistance is remarkably reduced during this loosening, the consumption of the electric power by the electric motor 17 for driving the take-up drum 13 can be suppressed. Further, the cuff ring 64 made of the same material as the conventional one being soft, but hardly stretchable can also be used.

Figure 16A:
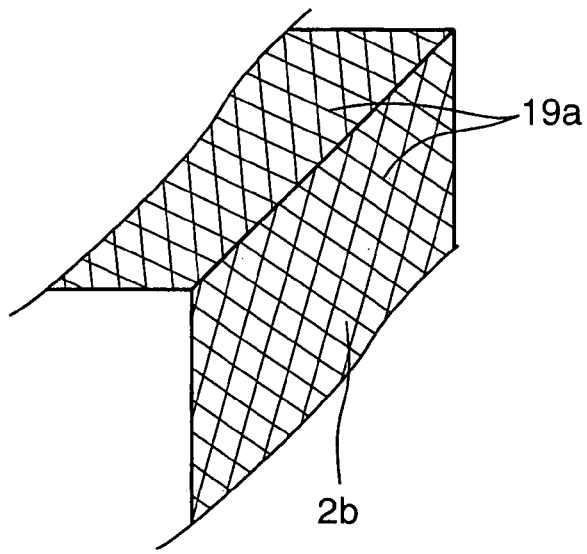
FIG. 16A is a perspective view showing an embossed sliding contact portion.

Since the cuff 12 is held in sliding contact with sliding contact portions 2d of the housing 2 as shown in FIG. 2A, the winding resistance is reduced by a treatment to better the slidability of the sliding contact portions 2d. Specifically, as shown in FIG. 16A, an embossed portion 19a (crosshatched portion) is entirely or partly formed on the surface of each sliding contact portion 2d. The embossed portion 19a is minute projections and recesses or unevenness formed on the outer surface of each sliding contact portion 2d, wherefore the cuff 12 is in contact only with the projections. Thus, friction between the inner surface of the housing 2 and the cuff 12 can be reduced to reduce the winding resistance.

Figure 16B:
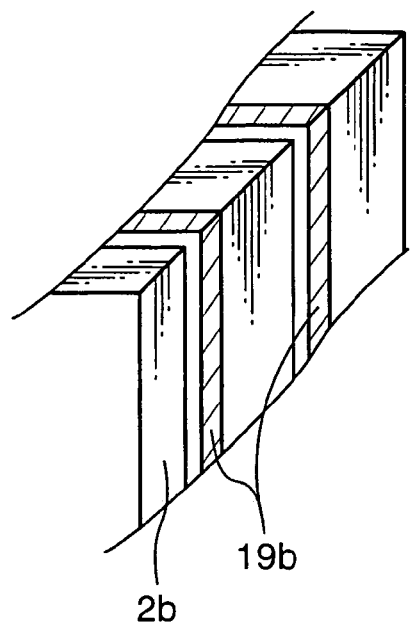
FIG. 16B is a perspective view showing a ribbed sliding contact portion.

Further, as shown in FIG. 16B, ribbed portions 19b may be entirely or partly formed on the surface of each sliding contact portion 2d. By forming the ribbed portions 19b, the cuff 12 is in contact only with the projected portions or ribs. Alternatively, tapes having a good lubricating property may be adhered to serve as portions treated to better the slidability thereof.

As described above, since the contact resistance of the cuff 12 with the sliding contact portions 2d is reduced by the portions 19a, 19b treated to better the slidability, the consumption of the electric power of the electric motor 17 for driving the take-up drum 13 can be suppressed.

Figure 17A:
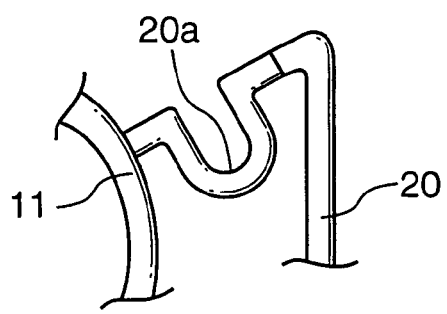
FIG. 17A is a side view showing a pump connecting tube formed with a U-shaped extensible portion.
Figure 17B:
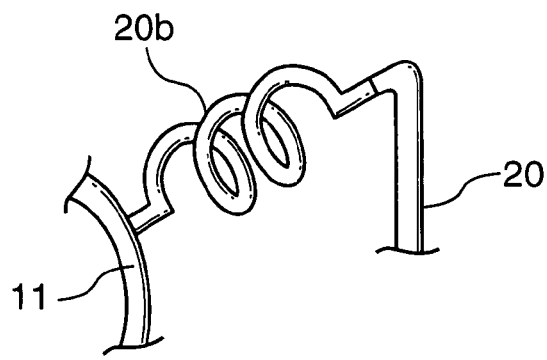
FIG. 17B is a side view showing a pump connecting tube formed with a spiral extensible portion.

FIG. 17A shows the construction of a connecting tube 20 for supplying an air to the blood flow blocking bag 11 of the cuff 12. The connecting tube 20 connects the blood flow blocking bag 11 and the pump. A portion of this connecting tube 20 connected with the blood flow blocking bag 11 is formed with an extensible portion 20a curved in U-shape. As shown in FIG. 17B, the portion of this connecting tube 20 connected with the blood flow blocking bag 11 may be formed with an extensible portion 20b wound in a spiral manner.

Since a tensile resistance of the connecting tube 19 during the winding and rewinding of the cuff 12 is reduced by the elongation and contraction of the extensible portion 20a, 20b, the consumption of the electric power of the electric motor 17 for driving the take-up drum 13 can be suppressed.

Figure 18:
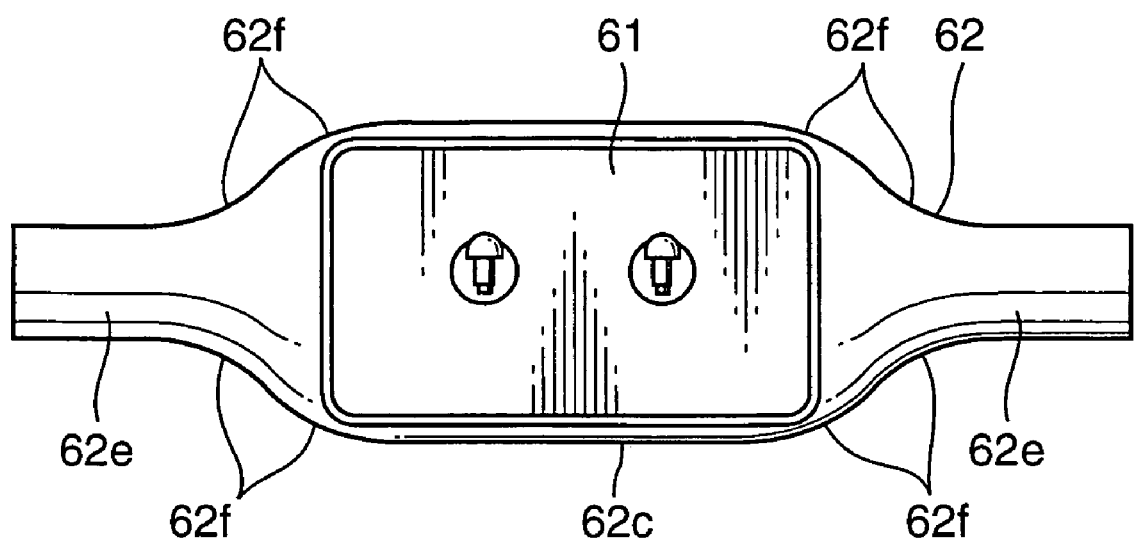
FIG. 18 is a plan view of a modification of the cuff formed with chamfered portions.

FIG. 18 shows a modified cuff 62 improved in view of the winding resistance. Chamfered portions 62f are formed on portions of the cuff 62 coupling the four corners of a blood flow blocking bag holding portion 62c and take-up portions 62e. Since a sliding resistance caused by the cuff 62 getting caught decreases by forming the chamfered portions 62e, the consumption of the electric power of the electric motor 17 for driving the take-up drum 13 can be suppressed.

The aforementioned constructions for reducing the winding resistance may be singly used or may be used in a suitable combination.

Figure 19A:
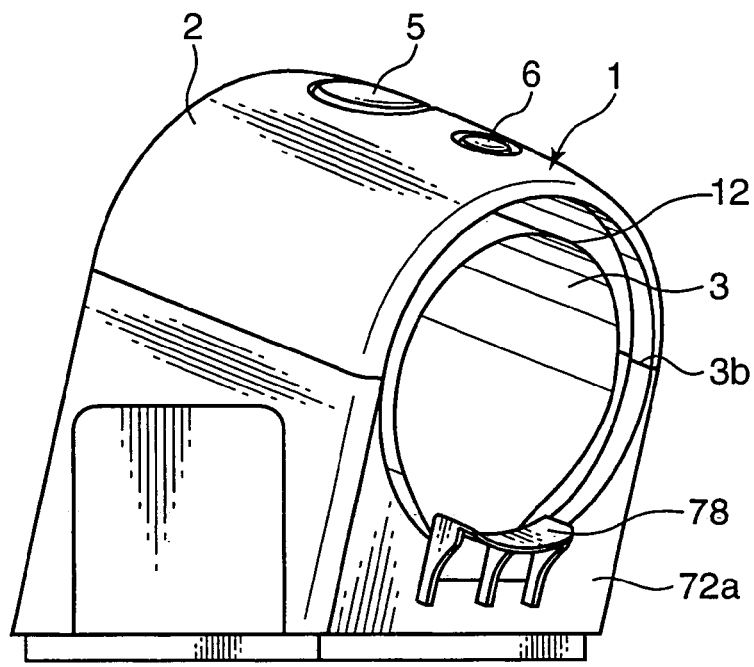
FIG. 19A is a perspective view showing the construction of a blood pressure monitor according to another modification.
Figure 19B:
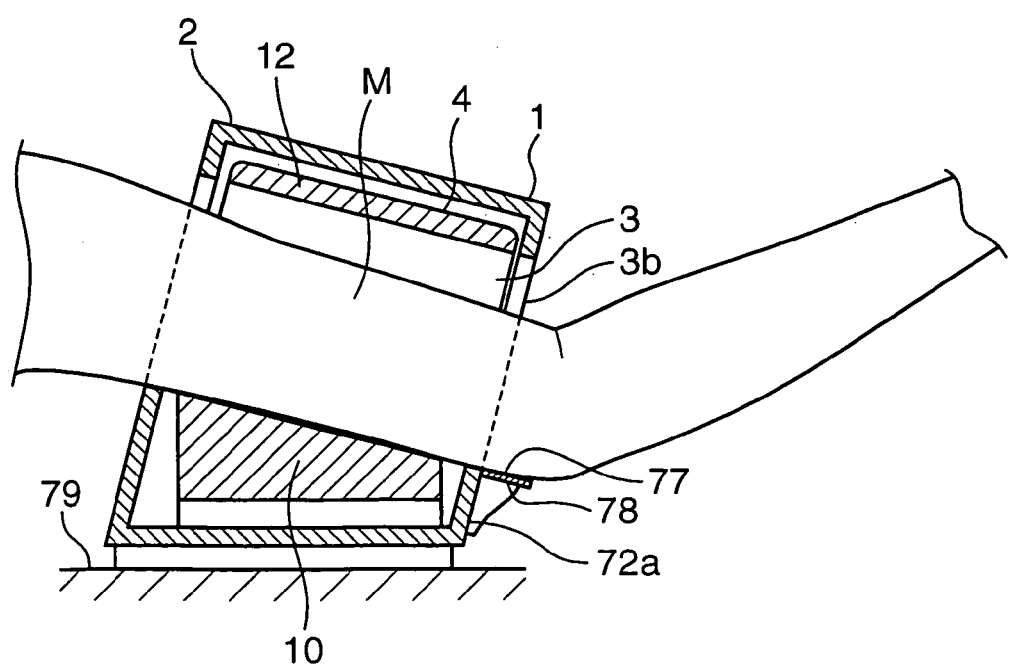
FIG. 19B is a sectional view of the blood pressure monitor of FIG. 19A.

Next, another modification of this embodiment is described. FIG. 19A is a perspective view showing the entire construction of this modification. In the following figures, the cuff ring 4 is not shown in order to clearly show the internal construction.

In this modification, an elbow support 78 is provided below the arm exit 3b on an exit-side wall 72a of the housing 2. The elbow support 78 projects from the exit-side wall 72a for placing an elbow 77 of the arm M inserted into the arm inserting hole 3.

By providing the elbow support 78 near the arm exit 3b of the arm inserting hole 3 of the housing 2 in this way, how much the arm M should be inserted into the arm inserting hole 3 can be known by placing the elbow 77 on the elbow support 78 when a measurer places the blood pressure monitor 1 on a table 79 or the like and inserts the arm M into the arm inserting hole 3. Thus, blood pressure can be constantly measured at a fixed measurement position, thereby improving reliability in measurement precision.

Further, the elbow support 78 does not take up much space because it is sufficient to provide it near the arm exit 3b of the arm inserting hole 3 of the housing 2.

In the case of placing the blood pressure monitor 1 on the table 79 or the like, an inserting angle of the arm M and the center of the arm inserting hole 3 may not agree depending on the height of the table 79 or the like, whereby the cuff 4 cannot be correctly wound around the arm M.

Figure 20A:
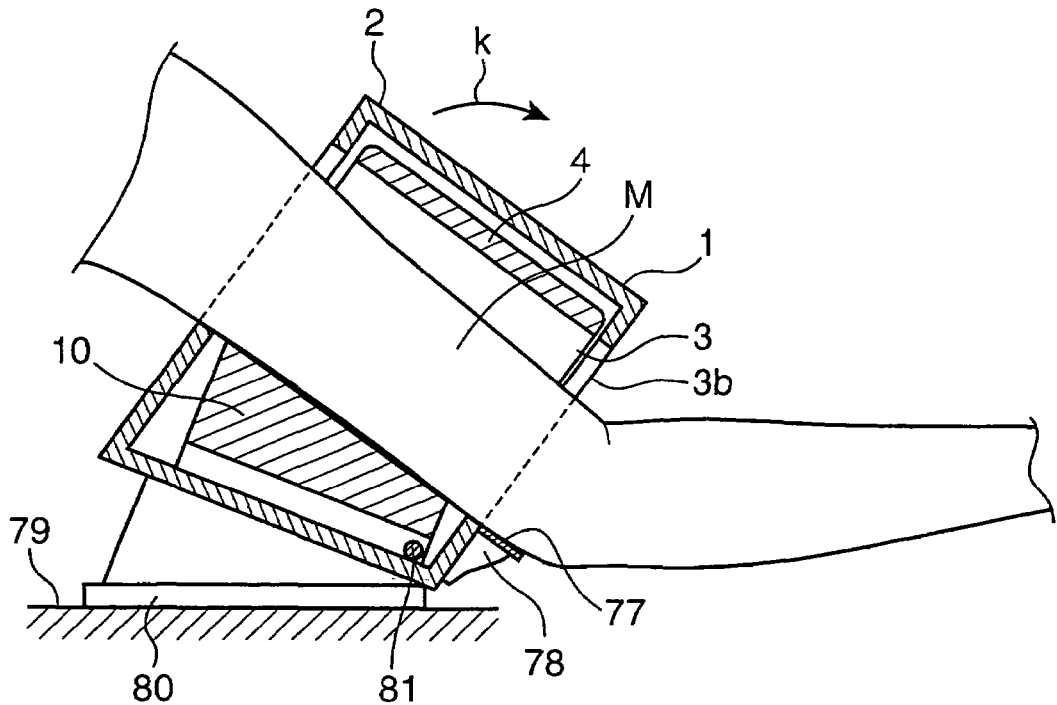
FIG. 20A is a sectional view showing a state where a housing is turned toward an arm exit side in the blood pressure monitor of FIG. 19A.

In view of this, as shown in FIG. 20A, a lower part of the housing 2 at the side of the arm exit 3b of the arm inserting hole 3 is supported on a base 80 of the blood pressure monitor 1 via a hinge member 81 to install the housing 2 rotatably toward an arm exit side (see arrow "k").

With this construction, when the measurer inserts the arm M into the arm inserting hole 3 and places the elbow 77 on the elbow support 78, the housing 2 is rotated toward the arm exit side by the weight of the elbow 77, whereby the inserting angle of the arm M comes to agree with the center of the arm inserting hole 3. Thus, the cuff 4 can be correctly wound around the arm M, thereby improving reliability in measurement precision.

Figure 20B:
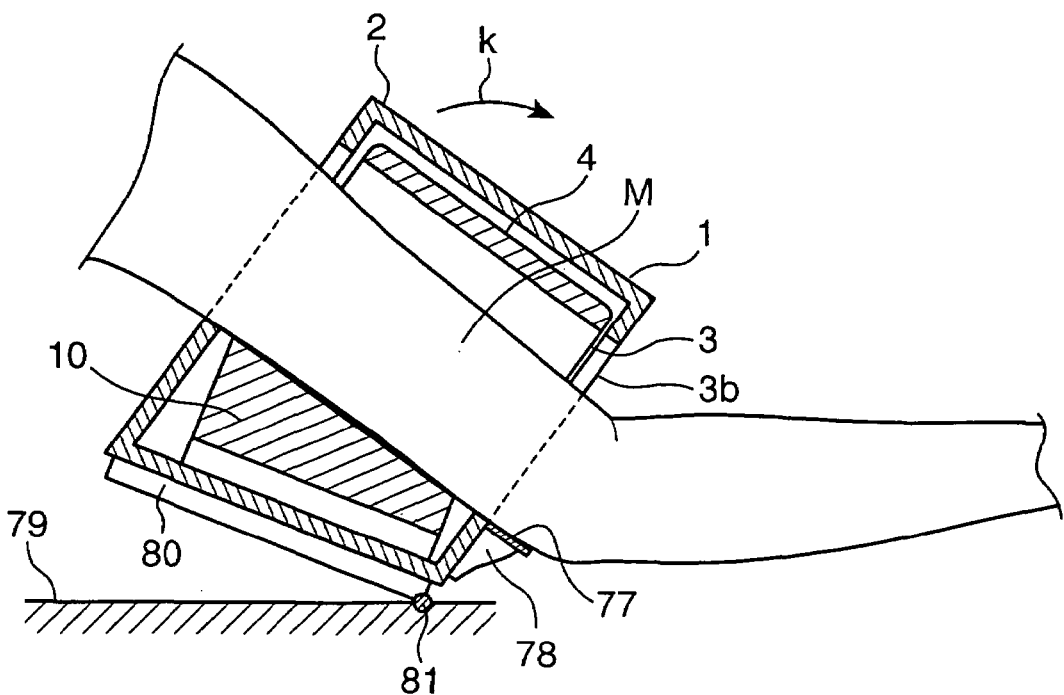
FIG. 20B is a sectional view showing a state where the entire blood pressure monitor is turned.

It should be noted that, as shown in FIG. 20B, the housing 2 and the base 80 can be installed rotatably toward the arm exit side (see arrow "k") by fixing the housing 2 and the base 80 to each other and supporting the base 80 on the table 79 or the like via the hinge member 81.

Figure 21A:
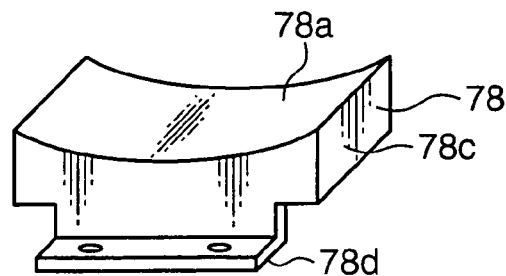
FIG. 21A is a perspective view showing an elbow support provided in the blood pressure monitor of FIG. 19A and formed with a concave surface.

If an elbow placing surface 78a is formed into a concave surface along transverse direction as shown in FIG. 21A, the elbow support 78 can be prevented from making transverse displacements when the elbow 77 is placed on the elbow support 78. Thus, a stable blood pressure measurement can be constantly carried out to reduce a variation in measurement precision.

Figure 21B:
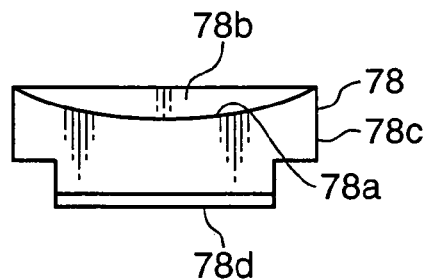
FIG. 21B is a front view of the elbow support showing a raised surface formed at an arm exit end.
Figure 21C:
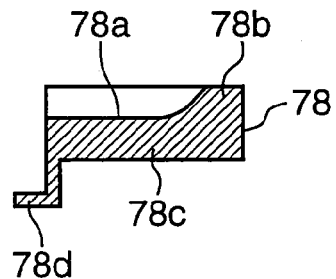
FIG. 21C is a sectional view of the elbow support showing the raised surface formed at the arm exit end.

Further, as shown in FIGS. 21B, 21C, a raised surface 78b may be formed at the arm exit side of the elbow placing surface 78a of the elbow support 78. Then, the placing position of the elbow 77 can be recognized by the feeling when the elbow 77 is placed on the elbow support 78, whereby displacements of the elbow 77 in arm exiting direction can be prevented. Thus, a stable blood pressure measurement can be constantly carried out to reduce a variation in measurement precision.

If the elbow support 78 is made of a soft material (e.g., a rubber material having a hardness of about 70 to 90), pain the elbow 77 possibly has upon being placed on the elbow support 78 can be mitigated.

In such a case, if an elbow placing portion 78c of the elbow support 78 is made of a soft material and a mounting portion 78d to the housing 2 is made of a hard material (e.g., a hard synthetic resin or a metal), the pain the elbow 77 possibly has upon being placed on the elbow support 78 can be mitigated and, simultaneously, a sufficient mounting force to the housing 2 can be ensured.

Although not specifically shown, the elbow support 78 may be formed by an inflatable and contractible air bag. With such a construction, the pain the elbow 77 possibly has upon being placed on the elbow support 78 made of the air bag can be mitigated and the elbow support 78 can be accommodated in a compact manner by letting the air bag contact.

Further, this construction is inexpensive because the air supplying pump and the air exhaust valve for the blood flow blocking bag built in the blood pressure monitor 1 can be used as means for supplying and discharging the air to and from the air bag to inflate and contact the air bag.

Figure 22:
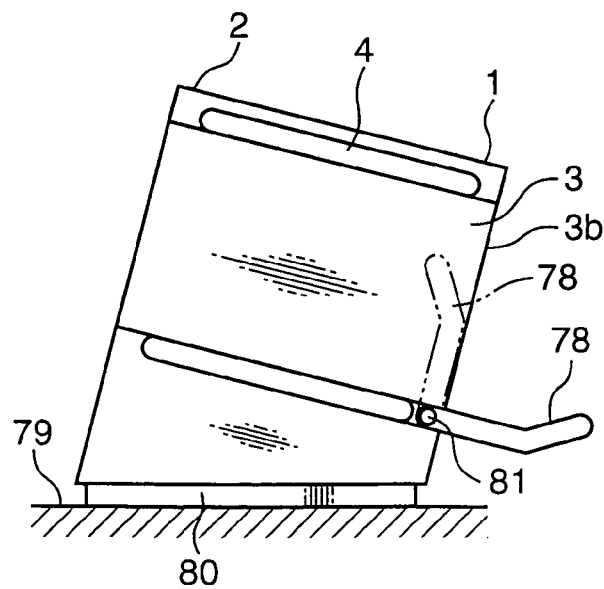
FIG. 22 is a sectional view showing that the elbow support is pivotal.

If the elbow support 78 is vertically pivotally supported at a position below the arm exit 3b of the arm inserting hole 3 via the hinge member 81 as shown in FIG. 22, the elbow support 78 can be folded toward the housing 2 when being not used (see phantom line). Thus, the elbow support 78 can be accommodated into the arm inserting hole 3 in a compact manner.

Figure 23A:
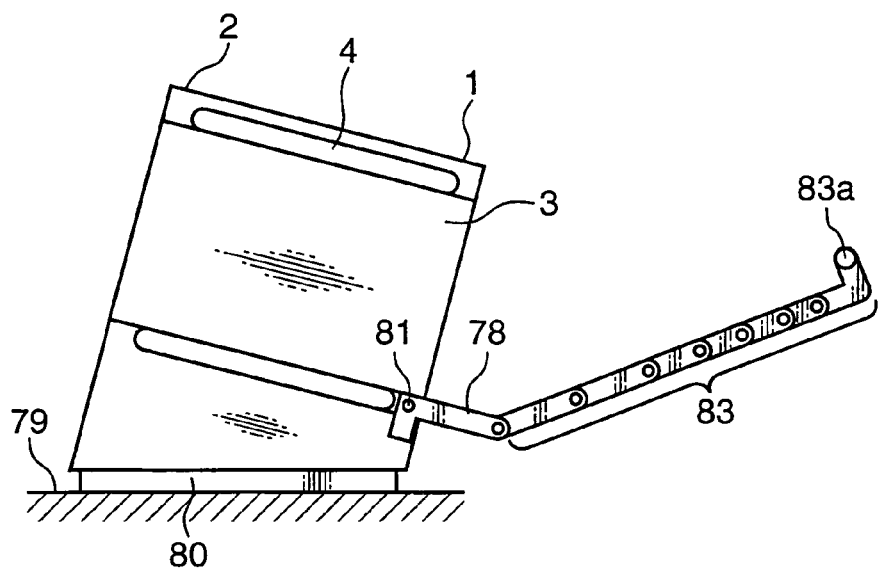
FIG. 23A is a sectional view of a blood pressure monitor having an lower arm support.

If a lower arm support 82 for placing a lower arm M2 is so provided as to be continuous with the elbow support 78 as shown in FIG. 23A, the arm can be entirely supported. Thus, the posture of the entire arm can be stabilized during the measurement.

Figure 23B:
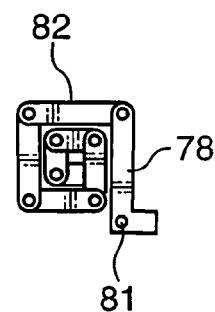
FIG. 23B is a side view showing the lower arm support in a folded state.

If the elbow support 78 is vertically pivotally supported via the hinge member 81 and the lower arm support 82 is formed such that respective sections are connected like a chain, the lower arm support 82 can be folded toward the housing 2 together with the elbow support 78 as shown in FIG. 23B. Thus, the elbow support 78 and the lower arm support 82 can be accommodated into the arm inserting hole 3 in a compact manner. The used lower arm support 82 whose sections are connected like a chain has such a construction that it can be bent at the respective joints with respect to a folding direction, but cannot be bent by the engagement of stoppers of the respective joints with respect to an extending direction.

Figure 24A:
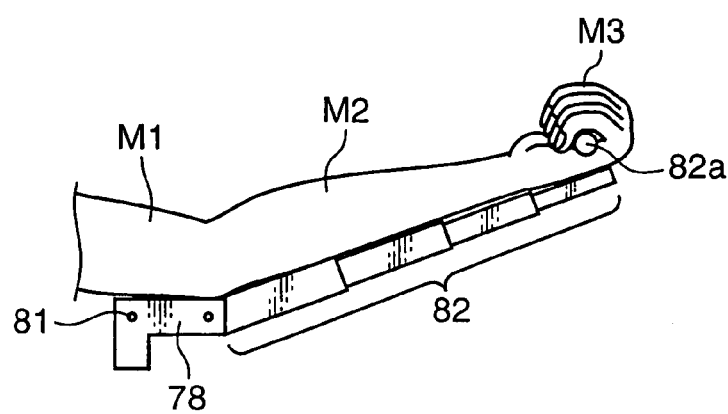
FIG. 24A is a side view of a modification of the lower arm support.

Further, as shown in FIG. 24A, the lower arm support 82 used may be an extensible rod.

Figure 24B:
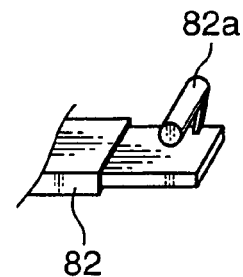
FIG. 24B is a perspective view showing a grip of the lower arm support of FIG. 24A.

If a grip 82a that can be gripped by a hand M3 is provided at the leading end of the lower arm support 82 as shown in FIGS. 23A and 24B, the palm (side of veins whose flow is desired to be blocked) of the hand M3 naturally faces up. Thus, blood pressure can be precisely measured.

Figure 25A:
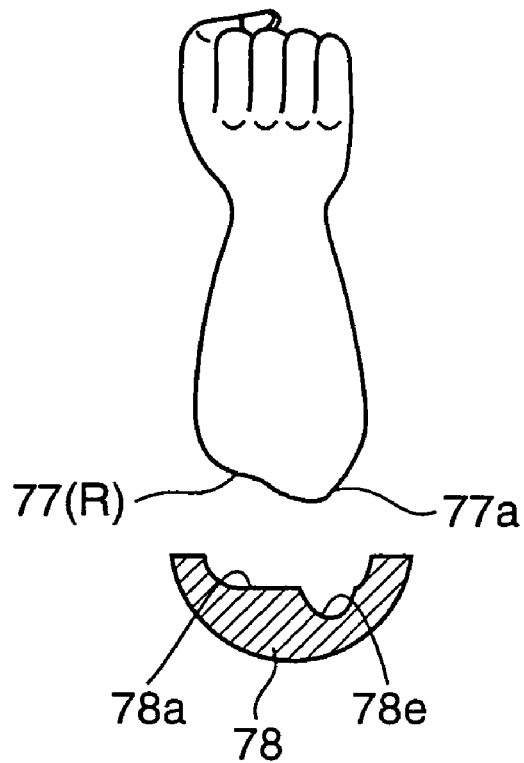
FIG. 25A is a front view showing a bone portion of a right elbow.
Figure 25B:
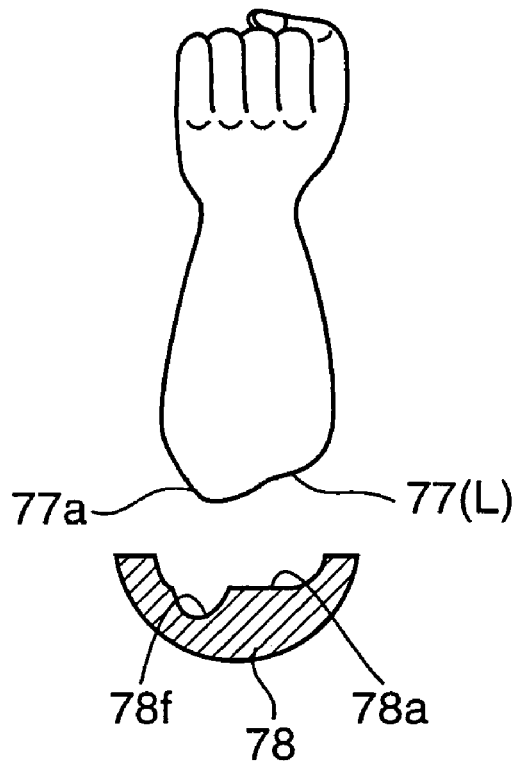
FIG. 25B is a front view showing a bone portion of a left elbow.

As shown in FIG. 25A, a bone portion 77a projecting from the elbow 77(R) is located at an inner side when the elbow 77(R) of the right arm is seen from front. Further, as shown in FIG. 25B, a bone portion 77a projecting from the elbow 77(L) is located at an inner side when the elbow 77(L) of the left arm is seen from front. Accordingly, if the elbow placing surface 78a of the elbow support 78 is flat, the position of the elbow 77(R, L) cannot be stably fixed due to the projecting bone portion 77a. Thus, if the measurement part is the right arm, a recess 78e in conformity with the bone portion 77a of the elbow 77(R) of the right arm may be formed in the elbow placing surface 78a of the elbow support 78 as shown in FIG. 25A. If the measurement part is the left arm, a recess 78f in conformity with the bone portion 77a of the elbow 77(R) of the left arm may be formed in the elbow placing surface 78a of the elbow support 78 as shown in FIG. 25B.

Figure 25C:
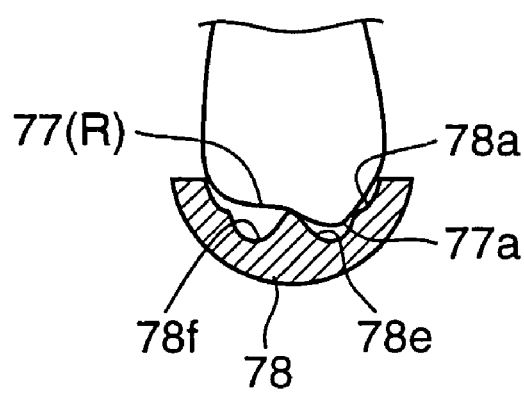
FIG. 25C is a front view when the right elbow is placed on an elbow support formed with recesses.
Figure 25D:
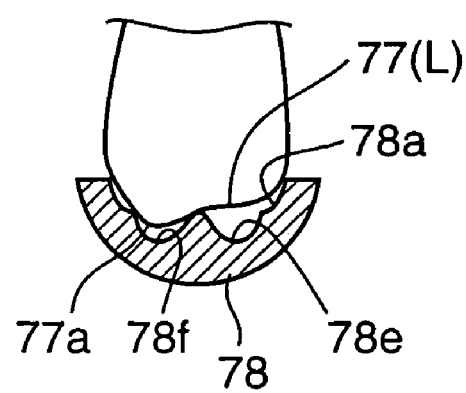
FIG. 25D is a front view when the left elbow is placed on the elbow support formed with the recesses.

However, since it cannot be known which of the left and right arms the measurer measures, the recesses 78e, 78f in conformity with the bone portions of the elbows 77(L, R) of the left and right arms are formed in the elbow placing surface 78a of the elbow support 78 as shown in FIG. 25C. Then, the bone portion 77a conforms to the recess 78e to stably fix the position of the elbow 77(R) if the elbow 77(R) of the right arm is placed on the elbow placing surface 78a of the elbow support 78 as shown in FIG. 25C while conforming to the recess 78f to stably fix the position of the elbow 77(L) if the elbow 77(L) of the left arm is placed on the elbow placing surface 78a of the elbow support 78 as shown in FIG. 25D.

If the elbow support 78 is made of an urethane having a low elasticity, the elbow support 78 fits the elbow 77(L, R) regardless of the shapes of the elbows 77(L, R) of the left and right arms even if the recesses 78e, 78f as above are not formed in the elbow placing surface 78a of the elbow support 78. Therefore, the position of the elbow can be stably fixed.

Figure 26A:
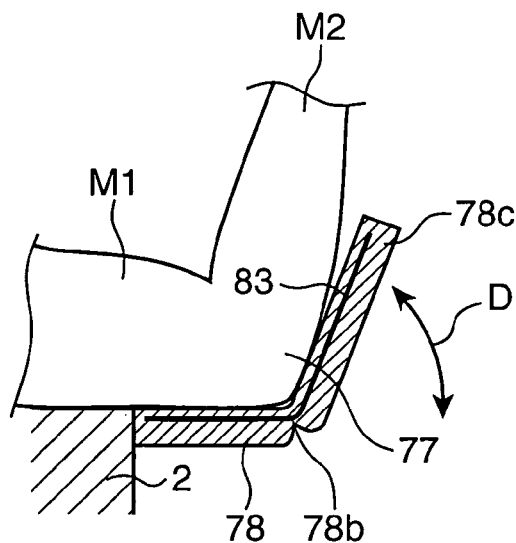
FIG. 26A is a side view of an elbow support having a rising portion.

As shown in FIG. 26A, a rising portion 78c that is so supported via a hinge portion 78b as to be vertically pivotal (see arrow "D") and can rise any time may be provided at the leading end of the elbow support 78. In order to cause the rising portion 78c to rise, a leaf spring 83 for biasing the rising portion 78c in rising direction is embedded in the elbow support 78 and the rising portion 78c by insert molding.

Figure 26B:
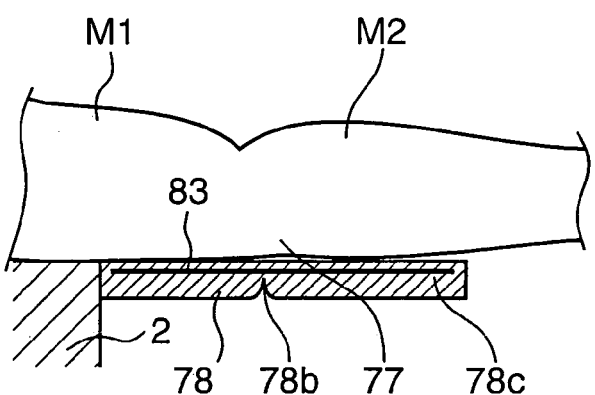
FIG. 26B is a side view of the elbow support having the rising portion laid down.
Figure 27:
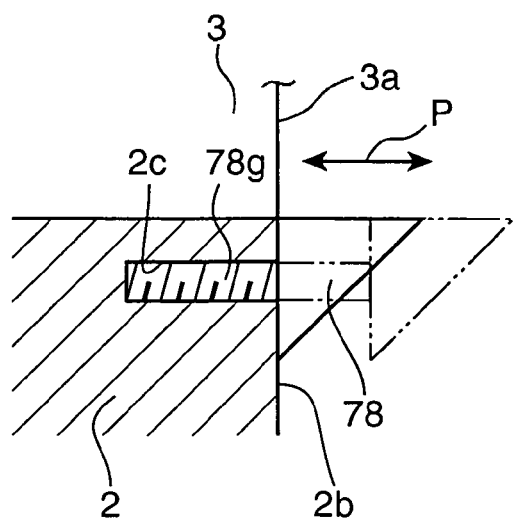
FIG. 27 is a sectional view of a position adjusting mechanism for the elbow support.

By providing the rising portion 78c at the leading end of the elbow support 78 in this way, the measurer can insert the arm into the arm inserting hole 3 to place the elbow 77 of the bent arm on the rising portion 78c, thereby positioning the elbow 77. If the elbow 77 is stretched thereafter as shown in FIG. 26B, the rising portion 78c lays down straight against a biasing force of the leaf spring 83, wherefore the elbow 77 does not come into contact with the rising portion 78c and a possible pain at the elbow 77 can be reduced.

The position of the arm M on the elbow support 78 with respect to inserting direction can be adjusted (see arrow "p") by forming an internally threaded portion 2c in a side wall 2b of the rear part of the housing 2 below the arm exit 3b of the arm inserting hole 3 and mounting a male screw 78g engageable with the internally threaded portion 2c on the elbow support 78 to change the engaged position of the male screw 2c. Beside the engagement of the internally threaded portion 2c and the male screw 78b, a click-stop construction or the like can be adopted. Accordingly, even if measurers whose arms M differ in length use this blood pressure monitor, the elbows 77 can be placed at proper positions.

If the elbow support 78 is so supported between the vicinity of the entrance of the arm inserting hole 3 and the vicinity of the exit thereof as to be movable along forward and backward directions, the arm M can be inserted into the arm inserting hole 3 together with the elbow support 78 with the elbow support 78 brought closer to the entrance of the arm inserting hole 3 and the elbow 77 placed on the elbow support 78. Thus, the elbow placing position is easy to see and, therefore, problems of excessively or insufficiently inserting the arm M into the arm inserting hole 3 can be solved.

Further, if the housing 2 is so supported on the base 80 as to be movable along the inserting direction of the arm and the elbow support 78 is mounted at a part of the base 80 corresponding to the vicinity of the entrance of the arm inserting hole 3 of the housing 2, the arm M can be inserted into the arm inserting hole 3 together with the elbow support 78 by moving the housing 2 with the elbow 77 placed on the elbow support 78. Thus, the elbow placing position is easy to see and, therefore, problems of excessively or insufficiently inserting the arm M into the arm inserting hole 3 can be solved. Further, since it is sufficient to move the housing 2 with the elbow 77 placed on the elbow support 78, the measurer can carry out a measurement in a natural posture without bending forward.

Furthermore, if a detector (e.g., switch or the like) for detecting that the measurer has placed the elbow 77 is provided in the elbow support 78, notification can be made by giving a notification sound or the like when the detector detects that the measurer has placed the elbow 77 on the elbow support 78. Thus, the measurer can recognize that the elbow 77 is placed at a suitable position and can carry out a measurement while feeling at ease. Further, an automatic measurement is possible by starting automatically taking up the cuff 12 and the like upon the detection by the detector.

As described above, an inventive blood pressure monitor is provided with a box-shaped housing having openings formed in left and right side walls; a cuff transversely arranged in the housing, including an arm entrance and an arm exit at the opposite left and right ends corresponding to the openings and having a blood flow blocking bag formed in a specified area; a cuff take-up drum for taking up the opposite ends of the cuff so that the blood flow blocking bag extends along an outer circumferential surface of the inserted arm at the time of a measurement; and a pump for supplying the compressed air to the blood flow blocking bag.

It is preferable to provide a fastening force adjusting construction for evening out the arm fastening forces at the parts of the cuff near the arm entrance side and the arm exit side.

The fastening force adjusting construction preferably includes a cylindrical take-up drum, and the cuff having, in its development, one longitudinal end thereof inclined in a first direction and having the other longitudinal end thereof inclined in a second direction intersecting with the first direction at a specified angle.

By forming the cuff to have the inclined opposite ends, the outward facing widthwise end of the cuff becomes longer while the inward facing widthwise end thereof becomes shorter when the drum having the opposite longitudinal ends of the cuff coupled thereto is rotated to take up the cuff. Accordingly, the cuff is wound substantially into a conical tube thicker at the outward facing end and thinner at the inward facing end. If the thicker side of the arm or the like is positioned at the outward facing end and the thinner side thereof is positioned at the inward facing side, there is no clearance between the cuff and the arm or the like. Thus, the arm or the like can be evenly pressed by the blood flow blocking bag, thereby improving the measurement precision. Further, it is inexpensive because the measurement part can be evenly pressed only by changing the outer shape of the cuff.

The first direction preferably intersects with the longitudinal axis of the take-up drum at right angles. This can prevent the cuff from being taken up while being displaced along the longitudinal direction of the drum when the cuff is wound onto the drum.

The fastening force adjusting construction may include a cuff rectangular in its development and a conical take-up drum. When the conical drum having the opposite ends of the cuff coupled thereto is rotated to take up the cuff, the cuff is wound substantially into a conical tube ticker at one widthwise end of the cuff corresponding to the thinner side of the drum and thinner at the other widthwise end thereof corresponding to the thicker side of the drum. Accordingly, if the thicker side of the arm or the like is positioned at the thinner side of the drum and the thinner side thereof is positioned at the thicker side of the drum, there is no clearance between the cuff and the arm or the like. Thus, the arm or the like can be evenly pressed by the blood flow blocking bag, thereby improving the measurement precision. Further, it is inexpensive because the measurement part can be evenly pressed only by changing the shape of the drum.

The fastening force adjusting construction preferably includes a cuff having a specified number of slits formed at the side corresponding to the arm entrance side. When the drum having the opposite ends of the cuff coupled thereto is rotated to take up the cuff, the cuff can be wound substantially into a conical tube thicker at the side having the slits and thinner at the side having no slit since one widthwise end of the cuff having the slits has a better stretchability along longitudinal direction than the other widthwise end of the cuff having no slit. Accordingly, if the thicker side of the arm or the like is positioned at the end of the cuff having the slits and the thinner side thereof is positioned at the end of the cuff having no slit, there is no clearance between the cuff and the arm or the like. Thus, the arm or the like can be evenly pressed by the blood flow blocking bag, thereby improving the measurement precision. Further, it is inexpensive because the measurement part can be evenly pressed only by forming the slits in the cuff.

The fastening force adjusting construction preferably includes a cuff having the opposite ends split into an arm entrance side and an arm exit side, and two take-up drums for independently taking up the end of the cuff at the arm entrance side and the end of the cuff at the arm exit side. When the drums coupled to the corresponding ends of the cuff split into two sections are rotated to take up the cuff, the opposite ends of the cuff split into two sections can be independently wound. Since the cuff can be wound substantially into a conical tube by continuing to take up the cuff by means of the drum at the thinner side of the arm or the like by the drum even after the take-up of the cuff by the drum at the thicker side of the arm or the like is stopped, there is no clearance between the cuff and the arm or the like. Thus, the arm or the like can be evenly pressed by the blood flow blocking bag, thereby improving the measurement precision.

It is preferable to provide a cuff ring in the form of a cylindrical tube transversely arranged inside the cuff and having an arm entrance and an arm exit at the opposite left and right ends communicating with the openings and made of a soft material, and an arm rest disposed below the cuff ring, and to mount a flexible auxiliary sheet longer along circumferential direction than the arm rest on the cuff ring or the arm rest. With this construction, if the opposite ends of the cuff are taken up by the automatic take-up mechanism with the arm inserted in the cuff ring and placed on the arm rest, the arm is pressed against the arm rest via the cuff ring while the blood flow blocking bag is wound around the arm via the cuff ring. At this time, the auxiliary sheet longer along circumferential direction than the arm rest is pressed against the cuff whose width becomes narrower as the cuff is taken up, whereby the opposite ends of the auxiliary sheet with respect to circumferential direction rise to cover the opposite sides of the arm inserted into the cuff ring. This can prevent the epidermis part of the arm from being pulled by the cuff being taken up to get in between the cuff ring and the lateral portions of the arm rest.

It is preferable to form a cuff ring with a bag-shaped accommodating portion and accommodate the auxiliary sheet in the bag-shaped accommodating portion. Since the auxiliary sheet is accommodated into the bag-shaped accommodating portion of the cuff ring, problems that the auxiliary sheet comes out of the cuff ring and the mount position thereof is displaced do not occur.

It is preferable to form projected and recessed portions at the edges of the auxiliary sheet toward the cuff in plan view. Since the projected and recessed portions are formed at the edges of the auxiliary sheet, only the projected portions come into contact with the cuff being taken up even if the edges of the auxiliary sheet come into contact with this cuff, thereby reducing a contact area. Thus, the winding resistance of the cuff is reduced, whereby the consumption of the electric power can be suppressed in such a case where an electric battery is used as a power supply for a motor or the like for driving the automatic take-up mechanism.

A resistance reducing construction for reducing resistance at the time of taking up the cuff by the cuff take-up drum may be provided. Since resistance at the time of taking up and rewinding the cuff is reduced by the resistance reducing construction, the consumption of the electric power can be suppressed in such a case where an electric battery is used as a power supply for a motor or the like for driving the automatic take-up mechanism.

The resistance reducing construction may include a cuff ring in the form of a cylindrical tube transversely arranged inside the cuff, having an arm entrance and an arm exit at the opposite left and right ends communicating with the openings, and made of a stretch material stretchable at least along transverse direction. Since the cuff ring largely stretches at least along its longitudinal direction, the resistance of the cuff ring decreases upon reducing the diameter of the cuff ring by the cuff at the time of taking up the cuff. Thus, the consumption of the electric power of the automatic take-up drum can be suppressed.

The resistance reducing construction may include a cuff ring transversely arranged inside the cuff, having an arm entrance and an arm exit at the opposite left and right ends communicating with the openings and having the side thereof toward the blood flow blocking bag loosened. Since the side of the cuff ring toward the blood flow blocking bag is largely loosened, the resistance of the cuff ring decreases upon reducing the diameter of the cuff ring by the cuff at the time of taking up the cuff. Thus, the consumption of the electric power of the automatic take-up drum can be suppressed.

The resistance reducer may be realized by forming sliding portions treated to better the slidability in the sliding contact portions of the housing with which the cuff comes into sliding contact. Since the contact resistance of the cuff is reduced by the sliding portions, the consumption of the electric power of the automatic take-up drum can be suppressed.

The resistance reducer may include an extensible portion formed in the connecting tube connecting the blood flow blocking bag and the pump. Since the tensile resistance of the connecting tube at the time of taking up and rewinding the cuff decreases due to the elongation and construction of the extensible portion, the consumption of the electric power of the automatic take-up drum can be suppressed.

The resistance reducer may be realized by chamfering the portions of the cuff coupling the blood flow blocking bag and the take-up ends. Since the sliding resistance of the cuff created upon getting caught is reduced by the chamfered portions, the consumption of the electric power of the automatic take-up drum can be suppressed.

It is preferable to provide an elbow support for supporting the elbow of the inserted arm near the arm exit. With this construction, how much the upper arm should be inserted into the arm inserting hole can be known when the measurer inserts the upper arm into the arm inserting hole. This enables blood pressure measurements to be constantly carried out at the fixed measurement position, thereby improving the reliability in measurement precision. Further, since it is sufficient to provide the elbow support only near the exit of the arm inserting hole of an arm insertion block, the elbow support may be provided in a compact manner.

The base for supporting the housing rotatably toward the arm exit side may be coupled to the part of the housing below the arm exit via the hinge member. With this construction, when the measurer places the elbow on the elbow support, the arm insertion block is rotated by the weight of the arm, thereby bringing the center of the arm insertion hole into agreement with the inserting angle of the upper arm. Thus, the cuff can be correctly wound around the upper arm, thereby improving the reliability in measurement precision.

The elbow support may be formed such that the elbow placing surface is a curved surface concave in section along widthwise direction. Since the elbow placing surface of the elbow support is formed into the curved surface concave in section along widthwise direction, lateral displacements of the elbow can be prevented when the elbow is placed on the elbow support. Thus, stable blood pressure measurements can be constantly carried out to reduce a variation in measurement precision.

The elbow support may be formed with a raised portion at the projecting end thereof. This enables the recognition of the elbow placing position by the feeling, thereby preventing displacements of the elbow in projecting direction. Thus, stable blood pressure measurements can be constantly carried out to reduce a variation in measurement precision.

The elbow support may be foldable toward the housing. Since the elbow support can be folded toward the arm insertion block, it can be accommodated at the side of the arm insertion block in a compact manner.

The lower arm supporting member for supporting the lower arm may be so provided as to be continuous with the elbow support and may be foldable toward the housing together with the housing. With this construction, the entire arm can be held in a stable posture during the measurement since it can be supported. Further, since the lower arm support can be folded toward the housing together with the elbow support, the elbow support and the lower arm support can be accommodated at the side of the arm insertion block in a compact manner.

The elbow placing surface of the elbow support may be formed with recesses in conformity with the bone of the elbow. This enables the position of the elbow to be stably fixed regardless of which of the left and right elbows is placed on the elbow support.

This application is based on patent application Nos. 2004-47492, 2004-47512, 2004-47551 and 2004-154565 filed in Japan, the contents of which are hereby incorporated by references.

As this invention may be embodied in several forms without departing from the spirit of essential characteristics thereof, the present embodiment is therefore illustrative and not restrictive, since the scope of the invention is defined by the appended claims rather than by the description preceding them, and all changes that fall within metes and bounds of the claims, or equivalence of such metes and bounds.

What is claimed is:

1. A blood pressure monitor, comprising:
a housing having openings formed in opposite side walls;
a cuff transversely arranged in the housing,
wherein the cuff has an arm entrance and an arm exit at opposite sides corresponding to the openings formed in the opposite side walls and configured to receive a human arm, and the cuff having a blood flow blocking bag formed in a portion of the cuff;
a cuff take-up drum that receives opposite ends of the cuff and is configured to rotate to take up opposite ends of the cuff such that the blood flow blocking bag extends along the non-uniform outer circumferential surface of an arm inserted into the blood pressure monitor when the cuff take-up drum takes up opposite ends of the cuff; and
a pump that supplies a compressed air to the blood flow blocking bag.

2. A blood pressure monitor according to claim 1, wherein the cuff and cuff take-up drum are configured to evenly distribute an arm fastening force of the cuff at the arm entrance and the arm exit when the cuff is taken up by the cuff take-up drum to fit around the inserted arm.

3. A blood pressure monitor according to claim 1, further comprising cuff guide that guides the cuff towards the cuff take-up drum and wherein one of the cuff and the cuff guide has projecting portions and the other has recessed portions that reduce the winding resistance caused by the cuff and the cuff take-up drum.

4. A blood pressure monitor according to claim 1, further comprising an elbow support provided near one side wall of the housing to support an elbow of the inserted arm,
wherein the elbow support is configured to be provided inside the housing when the elbow support is not in use.

5. A blood pressure monitor according to claim 4, further comprising a base coupled to a lower part of the blood pressure monitor at the one side wall of the housing via a hinge such that the housing pivots vertically about the hinge to change its inclination relative to the base.

6. A blood pressure monitor according to claim 1, wherein the cuff is configured to automatically assume a truncated generally conical shape adapted to fit the shape of the inserted arm when the cuff is taken-up by the cuff take-up drum.

7. A blood pressure monitor according to claim 1, wherein the cuff take up drum is driven by an electric motor.

8. A blood pressure monitor comprising:
a housing having openings formed in opposite side walls;
a cuff transversely arranged in the housing,
wherein the cuff has an arm entrance and an arm exit at opposite sides corresponding to the openings formed in the opposite side walls and configured to receive a human arm, and the cuff having a blood flow blocking bag formed in a portion of the cuff;
a cuff take-up drum that receives opposite ends of the cuff such that the blood flow blocking bag is configured to extend along the non-uniform outer circumferential surface of an arm inserted into the blood pressure monitor;
a pump that supplies compressed air to the blood flow blocking bag; and
wherein the take-up drum and the cuff are configured to evenly distribute an arm fastening force of the cuff, the take up drum having a generally cylindrical shape, and
the cuff has one longitudinal end inclined in a first direction and another longitudinal end inclined in a second direction that intersects with the first direction at a specified angle.

9. A blood pressure monitor, comprising:
a housing having openings formed in opposite side walls;
a cuff transversely arranged in the housing,
wherein the cuff has an arm entrance and an arm exit at opposite sides corresponding to the openings formed in the opposite side walls and configured to receive a human arm, and the cuff having a blood flow blocking bag formed in a portion of the cuff;
a cuff take-up drum that receives opposite ends of the cuff such that the blood flow blocking bag is configured to extend along the non-uniform outer circumferential surface of an arm inserted into the blood pressure monitor;
a pump that supplies a compressed air to the blood flow blocking bag;
a cuff ring having a generally cylindrical shape transversely arranged inside the cuff,
wherein an arm entrance and an arm exit provided at opposite ends of the cuff ring communicate with the openings formed in the opposite side walls of the housing;
an arm rest disposed at under the cuff ring; and
a flexible auxiliary sheet mounted on the cuff ring,
wherein a length of the flexible auxiliary sheet is longer in a circumferential direction than a length of the arm rest in a circumferential direction.

10. A blood pressure monitor comprising:
a housing having openings formed in opposite side walls;
a cuff transversely arranged in the housing,
wherein the cuff has an arm entrance and an arm exit at opposite sides corresponding to the openings formed in the opposite side walls and configured to receive a human arm, and the cuff having a blood flow blocking bag formed in a portion of the cuff;
a cuff take-up drum that receives opposite ends of the cuff such that the blood flow blocking bag is configured to extend along the non-uniform outer circumferential surface of an arm inserted into the blood pressure monitor;
a pump that supplies compressed air to the blood flow blocking bag; and
an elbow support provided in the housing near one side wall of the housing to support an elbow of the inserted arm,
wherein the elbow support is coupled to the housing in a manner such that the elbow support has a supporting position and a folded position.

* * * * *